(12) United States Patent
Tsuji et al.

(10) Patent No.: US 10,507,266 B2
(45) Date of Patent: Dec. 17, 2019

(54) CARTILAGE-DAMAGE TREATMENT AGENT AND METHOD FOR PRODUCING SAME

(71) Applicant: TWO CELLS Co., Ltd., Hiroshima-shi, Hiroshima (JP)

(72) Inventors: Koichiro Tsuji, Hiroshima (JP); Minoru Morikawa, Hiroshima (JP); Satoshi Maeda, Hiroshima (JP); Yui Kitayama, Hiroshima (JP); Aki Ohmori, Hiroshima (JP); Jin Chang Shao, Hiroshima (JP); Shinichi Hasegawa, Hiroshima (JP); Yukio Kato, Hiroshima (JP); Takashi Matsushita, Tokyo (JP); Masato Takao, Tokyo (JP); Shinya Miki, Tokyo (JP); Ken Innami, Tokyo (JP); Yasufumi Takahashi, Tokyo (JP)

(73) Assignee: TWO CELLS Co., Ltd., Hiroshima (JP)

(*) Notice: Subject to any disclaimer, the term of this patent is extended or adjusted under 35 U.S.C. 154(b) by 14 days.

(21) Appl. No.: 14/906,495

(22) PCT Filed: Aug. 1, 2014

(86) PCT No.: PCT/JP2014/070382
§ 371 (c)(1),
(2) Date: Jan. 20, 2016

(87) PCT Pub. No.: WO2015/016357
PCT Pub. Date: Feb. 5, 2015

(65) Prior Publication Data
US 2016/0166734 A1    Jun. 16, 2016

(30) Foreign Application Priority Data

Aug. 1, 2013 (JP) ................. 2013-160856

(51) Int. Cl.
| | |
|---|---|
| *A61L 27/38* | (2006.01) |
| *A61L 27/36* | (2006.01) |
| *A61K 35/28* | (2015.01) |
| *C12N 5/077* | (2010.01) |
| *A61L 27/54* | (2006.01) |
| *A01N 1/02* | (2006.01) |
| *C12N 5/0775* | (2010.01) |
| *A61K 35/32* | (2015.01) |

(52) U.S. Cl.
CPC ........ *A61L 27/3895* (2013.01); *A01N 1/0284* (2013.01); *A61K 35/28* (2013.01); *A61L 27/3654* (2013.01); *A61L 27/3834* (2013.01); *A61L 27/3852* (2013.01); *A61L 27/54* (2013.01); *C12N 5/0655* (2013.01); *C12N 5/0662* (2013.01); *A61K 35/32* (2013.01); *A61L 2300/412* (2013.01); *A61L 2300/414* (2013.01); *A61L 2430/06* (2013.01); *C12N 2501/10* (2013.01); *C12N 2501/11* (2013.01); *C12N 2501/12* (2013.01); *C12N 2501/135* (2013.01); *C12N 2501/15* (2013.01)

(58) Field of Classification Search
CPC ............. A61L 27/3895; A61L 27/3654; A61L 27/3852; A61L 27/54; A61L 27/3834; A61L 2300/412; A61L 2430/06; A61L 2300/414; A01N 1/0284; C12N 5/0662; C12N 5/0655; C12N 2501/12; C12N 2501/135; C12N 2501/15; C12N 2501/10; C12N 2501/11; A61K 35/28; A61K 35/32
See application file for complete search history.

(56) References Cited

U.S. PATENT DOCUMENTS

| | | | |
|---|---|---|---|
| 2002/0005205 A1 | 1/2002 | Barry | |
| 2007/0292949 A1 | 12/2007 | Duguya et al. | |
| 2008/0254019 A1 | 10/2008 | Kato et al. | |
| 2009/0041730 A1 | 2/2009 | Barry | |
| 2010/0178274 A1 | 7/2010 | Sekiya et al. | |
| 2010/0279412 A1 | 11/2010 | Kato et al. | |
| 2011/0212523 A1 | 9/2011 | Kato et al. | |
| 2012/0148548 A1 | 6/2012 | Barry | |
| 2012/0213745 A1 | 8/2012 | Duguya et al. | |
| 2012/0329087 A1 | 12/2012 | Tsuchiya et al. | |
| 2013/0131804 A1 | 5/2013 | Barry | |
| 2013/0273010 A1 | 10/2013 | Duguay et al. | |
| 2015/0216904 A1 | 8/2015 | Barry | |
| 2015/0267172 A1 | 9/2015 | Kato et al. | |

FOREIGN PATENT DOCUMENTS

| | | | | |
|---|---|---|---|---|
| CA | 2792802 A1 | * | 9/2011 | ........... C12N 5/0663 |
| CN | 101490245 A | | 7/2009 | |
| CN | 101643719 A | | 2/2010 | |
| EP | 1736173 | | 12/2006 | |
| EP | 1988159 | | 11/2008 | |

(Continued)

OTHER PUBLICATIONS

Sato et al. Direct transplantation of mesenchymal stem cells into the knee joints of Hartley strain guinea pigs with spontaneous osteoarthritis. Arthritis Research & Therapy 2012, 14:R31; p. 1-9 (Year: 2012).*

(Continued)

*Primary Examiner* — Taeyoon Kim
(74) *Attorney, Agent, or Firm* — Casimir Jones, S.C.; Robert A. Goetz

(57) ABSTRACT

A method according to the present invention for producing a cartilage-damage treatment agent, includes the steps of: (i) proliferating mesenchymal stem cells in a serum-free medium A containing an FGF, a PDGF, a TGF-β, an HGF, an EGF, at least one phospholipid and at least one fatty acid; and (ii) mixing the mesenchymal stem cells thus proliferated in the step (i), an isotonic preserving agent, and a cytoprotective agent. This method provides a cartilage-damage treatment agent which favorably regenerates a cartilage tissue.

5 Claims, 28 Drawing Sheets

(56) References Cited

FOREIGN PATENT DOCUMENTS

| | | |
|---|---|---|
| EP | 2545928 | 1/2013 |
| JP | 2004-507454 | 3/2004 |
| JP | 2006-122147 A | 5/2006 |
| JP | 2006-211920 A | 8/2006 |
| JP | 2010-501547 A | 1/2010 |
| WO | 01/35968 | 5/2001 |
| WO | 2005/012512 | 2/2005 |
| WO | 2005/94888 A1 | 10/2005 |
| WO | 2007/80919 A1 | 7/2007 |
| WO | 2008/023829 | 2/2008 |
| WO | 2010/55616 A1 | 5/2010 |
| WO | 2011/111787 A1 | 9/2011 |

OTHER PUBLICATIONS

Akmal et al. The effects of hyaluronic acid on articular chondrocytes. J Bone Joint Surg [Br] 2005;87-B:1143-9. (Year: 2005).*
Supartz FX (sodium hyaluronate). Seikagaku corporation. 2015; p. 1-2 (Year: 2015).*
European Search Report, EP Patent Application No. 14832325.6, dated Jul. 11, 2016, 9 pages.
Database WPI, Week 200635, Thomson Scientific, London, GB; AN 2006-337379 XP002759387 & JP2006-122147 A (Univ Hiroshima) May 18, 2006 (May 18, 2006) *abstract*, & Database EPODOC [Online] European Patent Office, The Hague, NL; XP002759388, Database accession No. jp-2004311487-A.
Nishimura, M. et al., "Synthesis and Degradation of Hyaluronan by Bone Marrow Mesenchymal Stem Cells: Effects of Hyaluronan on Mesenchymal Stem Cells" Clin. Rheumatol, 16: pp. 240-245, 2004.
International Search Report, International Patent Application No. PCT/JP2014/070382, dated Oct. 14, 2014.
Matsusue, Y. "Treatment for Articular Cartilage Damage" Knack & Pitfalls, 2005.
English Translation of International Preliminary Report on Patentability, International Patent Application No. PCT/JP2014/070382, dated Feb. 11, 2016.
Mohand-Kaci et al. "Optimized Hyaluronic Acid-Hydrogel Design and Culture Conditions for Preservation of Mesenchymal Stem Cell Properties" Tissue Engineering: Part C, 2013, vol. 19, No. 4, p. 288-298, Online Publication Date: Oct. 24, 2012.
Office Action for JP Patent Application No. 2015-529631, dated Jan. 10, 2017.
Shu-Mei, H. et al. "intra-articular injection of mesenchymal stem cells for treatment of meniscus injury" Chinese Journal of Tissue Engineering Research, Jun. 4, 2013, vol. 17. No. 23 pp. 4355-4362.
Kisiel, AH et al. "Isolation, characterization, and in vitro proliferation of canine mesenchymal stem cells derived from bone marrow, adipose tissue, muscle, and periosteum." American Journal of Veterinary Research, Aug. 2012, vol. 73 No. 8 pp. 1305-1317.
Horie, M. et al. "Implantation of Allogenic Synovial Stem Cells Promotes Meniscal Regeneration in a Rabbit Meniscal Defect Model" Journal of Bone &. Joint Surgery American, 2012, vol. 94 No. 8 pp. 701-712.
Horie, M. et al. "Intra-articular injected synovial stem cells differentiate into meniscal cells directly and promote meniscal regeneration without mobilization to distant organs in rat massive meniscal defect" Stem Cells, 2009, vol. 27 No. 4 pp. 878-887.
CN Office Action for CN Patent Application No. 201480041243.8, dated Jul. 4, 2018.

* cited by examiner (a)

(b)

(c)

(a)

(b)

(c)

2 mm

CARTILAGE-DAMAGE TREATMENT AGENT AND METHOD FOR PRODUCING SAME

TECHNICAL FIELD

The present invention relates to a cartilage-damage treatment agent and a method for producing the cartilage-damage treatment agent. The present invention further relates to an additive for a medium, a culturing medium, and a kit which are for use in the method, and a culture method using any one of the additive, the culturing medium, and the kit.

BACKGROUND ART

In joint sites such as knees, cartilage tissues present in a joint with mobility on an inner side of synovial membrane is made up of type II collagen, proteoglycan, water, etc. Such cartilage tissues are defined as articular cartilages (hyaline cartilages). On the other hand, cartilage tissues present outside joint sites contain, as constituents, more type I collagen than type II collagen.

The articular cartilage has a poor ability for repair. Accordingly, once the articular cartilage is damaged, it is almost impossible to naturally regenerate the articular cartilage. In cases where a patient has a traumatic damage of articular cartilage and repeatedly suffers a severe pain and/or hydrarthrosis, the patient is treated with an analgesic medication for oral administration and/or intra-articular injection of hyaluronic acid. However, these treatments are symptomatic treatments and not a curative treatment. Accordingly, a current general treatment method for the articular cartilage is a method in which the articular cartilage is surgically regenerated. Non-Patent Literature 1 discloses bone trepanation and osteochondral autograft transplantation. These are well-known as main surgical treatment methods.

The bone trepanation disclosed in Non-Patent Literature 1 is a method including the steps of (i) drilling a bone in a damaged cartilage region so as to cause bleeding from bone marrow and (ii) leading mesenchymal stem cells (MSCs) contained in the bone marrow to the damaged cartilage region, in expectation of regeneration of a cartilage and a tissue which is similar to the cartilage. This method can be easily implemented under arthroscopy, without sacrifice of tissues of a patient himself/herself. Therefore, this method is widely employed as a primary treatment method for cartilage damage in the world.

Herein, stem cells are cells having a self-replication ability and a differentiation ability. Well-known examples of such stem cells encompass embryonic stem cells (ES cells), induced pluripotent stem cells (iPS cells), and somatic stem cells. Examples of the somatic stem cells encompass hematopoietic stem cells, neural stem cells, and mesenchymal stem cells. The ES cells and the iPS cells have multipotency which allows the ES cells and the iPS cells to differentiate into any tissues. The hematopoietic stem cells have an ability to differentiate into blood cells, and the neural stem cells have an ability to differentiate into nerve cells. Further, the mesenchymal stem cells are present in tissues of bone marrow etc., and are known as stem cells which have multipotency to differentiate into adipose cells, bone cells, chondrocytes, and the like cells.

The osteochondral autograft transplantation disclosed in Non-Patent Literature 1 is a method in which a cylindrical mass including a bone and a cartilage is taken from a healthy region of autologous joint cartilage, and then autografted into a site of damage. This method allows repair at the site of damage with a transplanted hyaline cartilage and a fibro cartilage which is in a gap of the transplanted hyaline cartilage. However, it is a drawback of the method that tissues in the healthy region are damaged and an area for transplantation is limited.

Further, as another surgical treatment method for articular cartilage damage, autologous chondrocyte transplantation is known. This autologous chondrocyte transplantation is a method reported by Brittberg et al. in 1994. According to the method, a small amount of a cartilage tissue is obtained from an unloaded site of knee articular cartilage of a patient himself/herself and chondrocytes are isolated and monolayer-cultured. Then, thus cultured chondrocytes are transplanted to a site of cartilage damage.

As still another surgical treatment method for articular cartilage damage, a treatment method utilizing tissue engineering as disclosed in Patent Literature 1. In this treatment method, a cell source such as chondrocytes, stem cell, or like cells and a scaffold material are transplanted together with each other to a site of articular cartilage damage, and thereby regeneration of an articular cartilage is promoted.

Further, human stem cell clinical research of a "treatment method using a three-dimensional tissue-engineered construct derived from autologous synovial mesenchymal stem cells, for articular chondral lesions" (research plan approved on Jan. 25, 2012) is being implemented at Osaka University Hospital. The subject of this clinical research is patients with traumatic knee cartilage damage. In this clinical research, first, synovial membrane stem cells isolated from an intra-articular tissue are cultured. Then, a biological stimulus is given to thus cultured cells, so that a three-dimensional tissue fragment is obtained. Thereafter, the tissue fragment is transplanted to a site of cartilage damage.

CITATION LIST

Patent Literature

[Patent Literature 1]
Pamphlet of International Publication No. WO2005/012512 (Publication date: Feb. 10, 2005)

Non-Patent Literature

[Non-Patent Literature 1]
Orthopedic Surgery Knack and Pitfalls, Essential Points and Blind Sides of Knee Joint Surgery, Masahiro Kurosaka, 2005

SUMMARY OF INVENTION

Technical Problem

However, the above conventional treatment methods for articular cartilage damage with use of mesenchymal stem cells have the following problems.

That is, in the bone trepanation disclosed in Non-Patent Literature 1, a recent report reveals the following problems: (i) a cartilage tissue in a site having undergone treatment is replaced from a hyaline cartilage to a fibrocartilage over time, so that the cartilage tissue becomes susceptive to damage; and (ii) though a clinical condition is favorably improved for about two years after the treatment, a pain relapses after five or more years has elapsed, so that patient activity decreases. This means that a long-term effect of the treatment is difficult to expect. Moreover, in the bone trepanation disclosed in Non-Patent Literature 1, the bone drilled for causing blood to flow into a cartilage tissue will not be repaired.

Further, in the osteochondral autograft transplantation disclosed in Non-Patent Literature 1, a cartilage tissue in a healthy cartilage region needs to be sacrificed. However, the healthy cartilage region decreases with aging. Accordingly, in cases where a subject patient is a middle-aged or senior patient, it may be difficult to obtain a necessary amount of a cartilage tissue for the cartilage damage treatment. Further, in the osteochondral autograft transplantation disclosed in Non-Patent Literature 1, though a fresh graft obtained from a patient still keeps biological activity, the biological activity will be lost when the graft is frozen. Therefore, it is necessary to obtain a fresh graft from a patient for every transplantation. This increases the burden on patients.

Though the autologous chondrocyte transplantation is a treatment method which may solve the above problems in the bone trepanation and the osteochondral autograft transplantation, the autologous chondrocyte transplantation has not previously been approved in Japan as a health insurance treatment. However, in July of 2012, JACC (registered trademark) was approved in Japan. JACC is an autologous cultured cartilage obtained by culturing chondrocytes, which have been isolated from a cartilage tissue of a patient himself/herself and embedded in an atelocollagen gel. Similarly, Carticel (registered trademark) was approved in the United States in August of 1997, and further, ChondroCelect (registered trademark) in Europe in October of 2009. Accordingly, the autologous chondrocyte transplantation is attracting attention as a new treatment method for traumatic cartilage defects. However, for this treatment to be applied, (i) no other treatment should exist and (ii) a site of cartilage defect must have a cartilage defect area equal to or larger than 4 cm$^2$. Therefore, as to the autologous chondrocyte transplantation, an application range is highly limited.

Further, the treatment method disclosed in Patent Literature 1 requires time for regeneration of an articular cartilage. In addition, according to this treatment method, transplantation needs to be repeatedly carried out.

Furthermore, in the "treatment method using a three-dimensional tissue-engineered construct derived from autologous synovial mesenchymal stem cells, for articular chondral lesions", the autologous mesenchymal stem cells are cultured in a serum-containing medium and then used. Accordingly, it is necessary to obtain cells from patients. This increases the burden of the patients. In addition, there is a risk of cell contamination etc. which may be caused by the serum, as described later.

In cases where cells such as mesenchymal stem cells are to be used in treatment for articular cartilage damage, the cells are cultured prior to administration. In culturing the cells, presently, a medium in which animal serum (typically, 10% to 15% fetal bovine serum) is added is widely used. This serum is used as a nutrient supply for promoting growth and/or proliferation of cells outside a living body or as a supply source of a biologically active material such as hormone.

However, serum is very expensive. Further, components of serum vary in each lot because the serum is a natural product. This tends to result in variation in cell proliferation effect. Furthermore, it is necessary to purify cultured cells so as to remove serum-derived proteins and the like from the cultured cells. This makes production operations cumbersome. In addition, there is a risk of contamination of the cultured cells by unknown pathogens (viruses, pathogenetic prions, etc.) mixed in the serum.

The present invention is attained in view of the above problems. An object of the present invention is to provide a cartilage-damage treatment agent (i) capable of favorably regenerating a cartilage and (ii) containing mesenchymal stem cells cultured in a serum-free medium, and a method for producing the cartilage-damage treatment agent, and further to provide an additive for a medium, a culturing medium, and a kit which are for use in the method, and a culture method using any one of the additive, the culturing medium, and the kit.

Solution to Problem

A method according to the present invention for producing a cartilage-damage treatment agent, includes the steps of: (i) proliferating mesenchymal stem cells in a serum-free medium A containing an FGF, a PDGF, a TGF-β, an HGF, an EGF, at least one phospholipid and at least one fatty acid; and (ii) mixing the mesenchymal stem cells thus proliferated in the step (i), an isotonic preserving agent, and a cytoprotective agent.

A cartilage-damage treatment agent according to the present invention includes: mesenchymal stem cells cultured in a serum-free medium A containing an FGF, a PDGF, a TGF-β, an HGF, an EGF, at least one phospholipid and at least one fatty acid; an isotonic preserving agent; and a cytoprotective agent.

A culturing medium according to the present invention is a serum-free culturing medium for producing a cartilage-damage treatment agent, the serum-free culturing medium containing a serum-free additive for a medium according the present invention.

A culture method according to the present invention is a culture method for producing a cartilage-damage treatment agent, the culture method including the step of culturing mesenchymal stem cells in the serum-free culturing medium according to the present invention.

A kit according to the present invention includes at least the serum-free additive for a medium according to the present invention.

Advantageous Effects of Invention

A method according to the present invention for producing a cartilage-damage treatment agent, includes the steps of: (i) proliferating mesenchymal stem cells in a serum-free medium A containing an FGF, a PDGF, a TGF-β, an HGF, an EGF, at least one phospholipid and at least one fatty acid; and (ii) mixing the mesenchymal stem cells thus proliferated in the step (i), an isotonic preserving agent, and a cytoprotective agent. Accordingly, the method of the present invention advantageously makes it possible to produce a cartilage-damage treatment agent (i) capable of favorably regenerating a cartilage at a site of cartilage damage and (ii) containing mesenchymal stem cells cultured in a serum-free medium.

DESCRIPTION OF EMBODIMENTS

Figure 1:
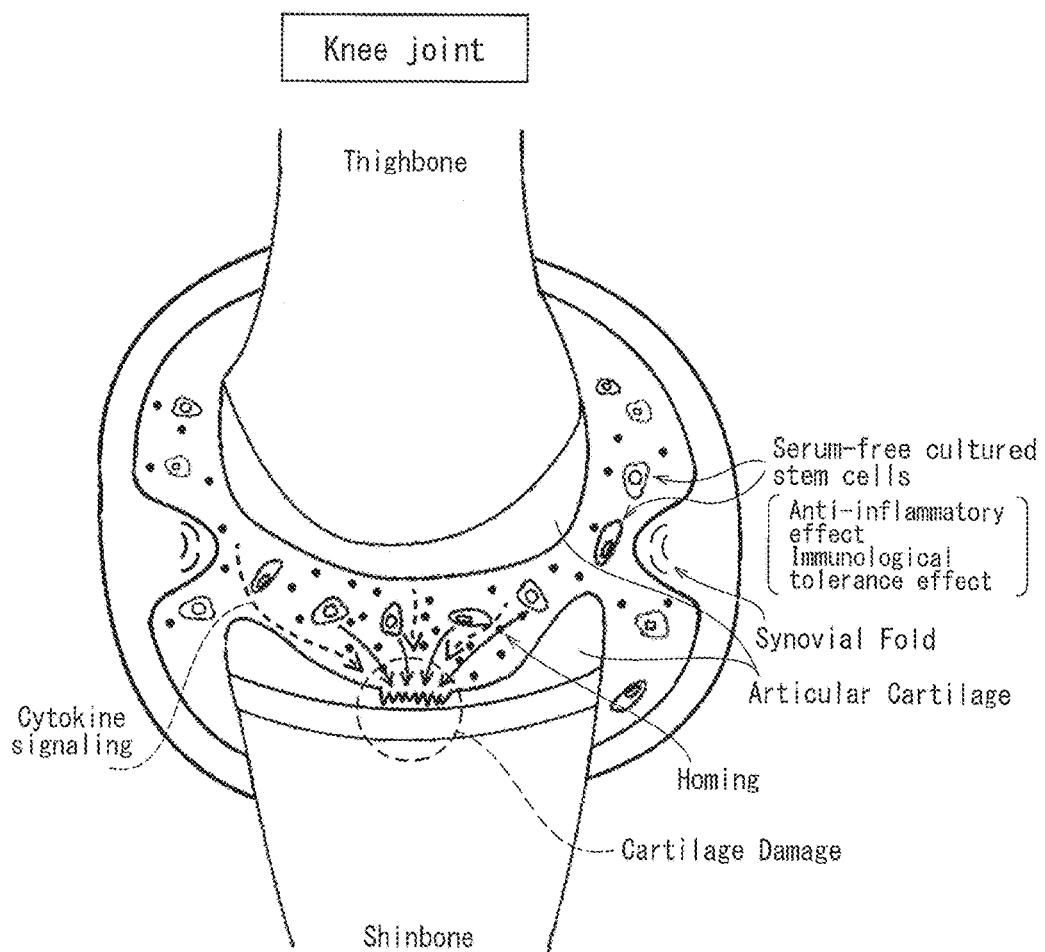
FIG. 1 is a schematic view illustrating a mechanism of the present invention.

1. Method for Producing Cartilage-Damage Treatment Agent

The present invention provides a method for producing a cartilage-damage treatment agent containing mesenchymal stem cells. The method according to the present invention for producing a cartilage-damage treatment agent includes: (i) a proliferation step of proliferating mesenchymal stem cells in a serum-free medium A containing an FGF, a PDGF, a TGF-β, an HGF, an EGF, at least one phospholipid and at least one fatty acid; and (ii) a mixing step of mixing the mesenchymal stem cells thus proliferated in the step (i), an isotonic preserving agent, and a cytoprotective agent.

The term "serum-free medium" as used herein means a medium which does not contain serum, and the term "serum-free culturing" as used herein means culturing without serum.

The term "cartilage-damage treatment agent" as used herein is a therapeutic agent, which is obtained by formulation of mesenchymal stem cells and used as a material for cartilage damage treatment in regenerative medicine etc. The cartilage-damage treatment agent can also be called a cartilage tissue regenerating agent. The cartilage-damage treatment agent encompasses not only an agent obtained by formulation of the mesenchymal stem cells in a manner such that in the agent, the mesenchymal stem cells remain as they are and functions of the mesenchymal stem cells are unchanged, but also an agent obtained by formulation of cells whose functions such as a differentiation ability are improved by culturing and proliferating the mesenchymal stem cells under a specific condition.

(Proliferation Step)

In the proliferation step, the mesenchymal stem cells are cultured in a serum-free medium A containing an FGF, a PDGF, a TGF-β, an HGF, an EGF, at least one phospholipid, and at least one fatty acid, so that the mesenchymal stem cells are proliferated.

<Mesenchymal Stem Cells>

The mesenchymal stem cells encompasses not only cells isolated from adult tissues of synovial membrane cells, adipose cells, bone marrow, an alveolar bone, a periodontal membrane, and the like but also cells isolated from various cells etc. of placenta, cord blood, and fetus. The mesenchymal stem cells to be proliferated in the proliferation step are preferably derived from tissues selected from the group consisting of synovial membrane, umbilical cord, cord blood, amnion, bone marrow, and adipose tissues.

The mesenchymal stem cells to be proliferated in the proliferation step are preferably cells of a patient himself/ herself to whom the cartilage-damage treatment agent to be produced as a result will be administered. Alternatively, the mesenchymal stem cells may be allogeneic cells. Further, the mesenchymal stem cells to be proliferated in the proliferation step may be human mesenchymal stem cells or alternatively mesenchymal stem cells derived from non-human animals such as mice, rats, cats, dogs, etc.

It is possible to employ a conventionally publicly-known method as a method for isolating mesenchymal stem cells from tissues. For example, the mesenchymal stem cells can be favorably isolated from tissues by a collagenase method.

<Serum-Free Medium A>

A basal medium for constituting the serum-free medium A for use in the proliferation step is not particularly limited, provided that the basal medium is a well-known medium for animal cells in this field. A preferable examples of the basal medium encompass a Ham's F12 medium, a DMEM medium, an RPMI-1640 medium, and an MCDB medium. Such basal mediums each may be used alone, or two or more of such basal mediums may be used in combination. A basal medium for constituting the serum-free medium A in one embodiment is preferably a medium in which an MCDB medium and a DMEM medium are mixed at a ratio of 1:1.

In one embodiment, the serum-free medium A obtained by adding an FGF, a PDGF, a TGF-β, an HGF, an EGF, at least one phospholipid, and at least one fatty acid to the basal medium may be used in the proliferation step.

A content of the FGF in the basal medium is preferably 0.1 to 100 ng/mL at a final concentration, and more preferably 3 ng/mL. A content of the PDGF in the basal medium is preferably 0.5 to 100 ng/mL at a final concentration, and more preferably 10 ng/mL. A content of the TGF-β in the basal medium is preferably 0.5 to 100 ng/mL, and more preferably 10 ng/mL.

A content of the HGF in the basal medium is preferably 0.1 to 50 ng/mL at a final concentration, and more preferably 5 ng/mL. A content of the EGF in the basal medium is preferably 0.5 to 200 ng/mL at a final concentration, and more preferably 20 ng/mL. A total content of phospholipid(s) in the basal medium is preferably 0.1 to 30 μg/mL at a final concentration, and more preferably 10 μg/mL. A total content of fatty acid(s) in the basal medium is preferably 1/1000 to 1/10 of the basal medium, and more preferably 1/100.

The use of such a serum-free medium A has a proliferation promoting effect, which is equivalent to or better than that of a serum-containing medium, while preventing heteroprotein contamination. This makes it possible to desirably proliferate the mesenchymal stem cells.

Examples of the phospholipid contained in the serum-free medium A encompass phosphatidic acid, lysophosphatidic acid, phosphatidylinositol, phosphatidyl serine, phosphatidyl ethanolamine, phosphatidyl choline, and phosphatidyl glycerol. Such phospholipids each may be used alone, or two or more of such phospholipids may be used in combination. In one embodiment, the serum-free medium A may contain phosphatidic acid and phosphatidyl choline in combination, and these phospholipids may be derived from animals or plants.

Examples of the fatty acid contained in the serum-free medium A encompass linoleic acid, oleic acid, linolenic acid, arachidonic acid, myristic acid, palmitoleic acid, palmitic acid, and stearic acid. Such fatty acids each may be used alone or two or more of such fatty acids may be used in combination. Further, in one embodiment, the serum-free medium A may contain not only the fatty acid(s) but also cholesterol.

The term "FGF" as used herein means a growth factor selected from a fibroblast growth factor (FGF) family, and is preferably FGF-2 (bFGF). However, other FGFs of the FGF family, such as FGF-1, may also be selected.

The term "PDGF" as used herein means a growth factor selected from a platelet derived growth factor (PDGF) family, and is preferably PDGF-BB or PDGF-AB.

The term "TGF-β" as used herein means a growth factor selected from a transforming growth factor-β (TGF-β) family, and is preferably TGF-β3. However, other TGF-βs of the TGF-β family may also be selected.

The term "HGF" as used herein means a growth factor selected from a hepatocyte growth factor family, and the term "EGF" as used herein means a growth factor selected from an epidermal growth factor (EGF) family.

In one embodiment, the serum-free medium A may further contain at least two factors selected from the group consisting of a connective tissue growth factor (CTGF), a vascular endothelial growth factor (VEGF), and an ascorbic acid compound.

The term "ascorbic acid compound" as used herein means ascorbic acid (vitamin C), ascorbic acid-2-phosphate, or a compound similar to these ascorbic acids.

Note that the growth factors contained in the serum-free medium A may be naturally-occurring ones or may be ones produced by gene modification.

In one embodiment, the serum-free medium A preferably contains a lipid antioxidant. The lipid antioxidant contained in the serum-free medium A may be DL-α-tocopherol acetate (vitamin E) in one embodiment. The serum-free medium A may further contain a surfactant. The surfactant contained in the serum-free medium A may be Pluronic F-68 or Tween 80 in one embodiment.

The serum-free medium A may further contain insulin, transferrin, and selenate. The term "insulin" as used herein may mean an insulin-like growth factor, and may be derived from a natural cell or may be produced by gene modification. The serum-free medium A may further contain dexamethasone, or another glucocorticoid.

In the proliferation step, the mesenchymal stem cells isolated from an animal tissue or cell (e.g., human tissue or cell) by a conventionally publicly-known method is inoculated into the serum-free medium A described above, and is cultured until the mesenchymal stem cells are proliferated to the desired number of cells. As a culture condition, preferably, the mesenchymal stem cells ($1 \times 10^4$ to $2 \times 10^4$) are inoculated into a medium (1 mL). As other culture conditions, it is preferable that: a culture temperature be 37° C.±1° C.; a culture time be in a range of 48 to 96 hours; and a culture environment be under 5% $CO_2$. By culturing the mesenchymal stem cells under the above condition, it is possible to efficiently produce a large number of mesenchymal stem cells whose differentiation ability is maintained.

In the proliferation step, a culture vessel for use in culturing is not particularly limited, provided that the mesenchymal stem cells can be proliferated in the culture vessel. For example, a 75 $cm^2$ flask (Falcon), a 75 $cm^2$ flask (manufactured by SUMITOMO BAKELITE CO., LTD.), or the like can be suitably used. Note, however, that proliferation of some cells may be affected by a kind of a culture vessel used. It is therefore preferable that, in order to proliferate more efficiently the mesenchymal stem cells, the mesenchymal stem cells to be proliferated (hereinafter, also referred to as a "proliferation target cells") in the proliferation step is subjected to the proliferation step by use of a culture vessel suitable for proliferation of these mesenchymal stem cells.

Examples of a method for selecting a culture vessel suitable for proliferation of proliferation target cells encompass a method in which an optimum culture vessel is selected by the proliferation target cells. More specifically, multiple kinds of culture vessels are prepared, and proliferation target cells are proliferated under the same condition except the kinds of culture vessels. After two weeks from the start of culturing, the number of cells in each vessel is measured by a publicly-known method. Then, it can be determined that a culture vessel having the largest number of cells is the most suitable for proliferating the proliferation target cells. Further, in a case where the proliferation speed of the proliferation target cell is high, it can be determined, even before two weeks from the start of the culturing, that a culture vessel which takes the shortest period before the number of the proliferation target cells reaches 80% to 90% of the number of cells in a confluent state is the most suitable for proliferating the proliferation target cells.

Note that adhesion of the mesenchymal stem cells to a culture vessel is an essential condition in proliferation of the mesenchymal stem cells. It is therefore preferable that, in a case where the proliferation target cells insufficiently adhere to the culture vessel, the serum-free medium A further contains cell adhesion molecules in the proliferation step. Examples of the cell adhesion molecules encompass fibronectin, collagen, and gelatin. Each type of these cell adhesion molecules may be used alone, or two or more types of the cell adhesion molecules may be used in combination.

In the serum-free medium A, a cell adhesion molecule content is preferably 1 to 50 μg/mL at a final concentration, and more preferably 5 μg/mL at the final concentration. In one embodiment, in a case where the cell adhesion molecules are fibronectin, fibronectin is added so that a final concentration of fibronectin in the serum-free medium A is 5 μg/mL. This can improve the adhesion efficiency of the proliferation target cells with respect to the culture vessel.

Alternatively, the proliferation target cells may be proliferated by use of a culture vessel coated with the cell adhesion molecules.

In the proliferation step, the mesenchymal stem cells may be subcultured at least once. The mesenchymal stem cells are proliferated scaffold-dependently. For example, in a case where the mesenchymal stem cells are locally unevenly proliferated or a like case, the culture condition of the mesenchymal stem cells can be improved by subculturing the mesenchymal stem cells in the process of the proliferation step.

The subculturing of the mesenchymal stem cells may be carried out in any way, and may be performed by a conventionally publicly-known method of subculturing mesenchymal stem cells. For the sake of good cell conditions of subcultured mesenchymal stem cells, it is preferable to detach the mesenchymal stem cells by use of a cell detachment agent which does not contain any component derived from mammals and microorganisms, in a case where the mesenchymal stem cells are to be subcultured in the proliferation step. Examples of the cell detachment agent which does not contain any component derived from mammals and microorganisms encompass ACCUTASE (registered trademark) (Innovative Cell Technologies, Inc.), and TrypLE (registered trademark) Select (1X) (Life Technologies Corporation).

The following discusses an example of a subculturing method in a case where ACCUTASE is used as cell detachment agent which does not contain any component derived from mammals and microorganisms. The mesenchymal stem cells are detached and subcultured by a procedure including the steps (i) to (vi). Note that, the following subculturing method is assumed to use a T-25 flask (Falcon) as a culture vessel.
(i) Wash a cell layer with PBS(−) (i.e., PBS without calcium and magnesium) (5 mL).
(ii) Add ACCUTASE (2 mL).
(iii) Let the resultant liquid stand at a room temperature for about two minutes, and check that cells are detached. Thereafter, transfer a cell suspension fluid to a centrifuging tube.
(iv) Add PBS(−) (7 mL) into a culture vessel, and rinse a bottom surface of the flask with PBS(−).
(v) Transfer the resultant solution of the step (iv) to the centrifuging tube in the step (iii), and centrifuge the solution at 1500 rpm (200×g) for five minutes.
(vi) Remove supernatant, and inoculate cells into the serum-free medium A at an inoculation density of 5,000 cells/$cm^2$.

Note that, in the proliferation step, it is preferable to provide mesenchymal stem cells which have been subcultured at least once (P1) after collection of the mesenchymal stem cells from animal tissues (such as human tissues).

Further, in the proliferation step, it is preferable to proliferate the mesenchymal stem cells while a differentiation ability is maintained. In other words, in the proliferation step, undifferentiated mesenchymal stem cells having a differentiation ability to differentiate into adipose cells, bone cells, chondrocytes, etc. are cultured in the serum-free medium A. Further, thus cultured mesenchymal stem cells are also undifferentiated and have a differentiation ability. This makes it possible to produce a cartilage-damage treatment agent containing mesenchymal stem cells having a differentiation ability. Then, the mesenchymal stem cells maintaining a differentiation ability can be administered to a site of cartilage damage by administration of the cartilage-damage treatment agent to the site of cartilage damage.

Note that whether or not the mesenchymal stem cells have a differentiation ability can be checked by (i) culturing proliferated mesenchymal stem cells in mediums such as an osteoblast differentiation medium, an adipocyte differentiation medium, a chondrocyte differentiation medium, and the like and (ii) assessing whether or not differentiation of the proliferated mesenchymal stem cells into osteoblasts, adipose cells, chondrocytes, and the like is induced. Alternatively, it is possible to check whether or not the mesenchymal stem cells has a differentiation ability by (a) a method in which expression of surface antigens is assessed by reacting the proliferated mesenchymal stem cells with various CD antibodies and measuring fluorescence intensities by use of a flow cytometer, (b) a method in which expression of undifferentiation marker genes is assessed by measuring undifferentiation marker genes (nanog, sox2, and oct3/4) and an endogenous control gene (Gapdh) in the proliferated mesenchymal stem cells, or the like method.

(Mixing Step)

In the mixing step, the mesenchymal stem cells after the proliferation step, the isotonic preserving agent, and the cytoprotective agent are mixed, so that a cell administration solution is prepared. This cell administration solution is the cartilage-damage treatment agent.

The mesenchymal stems cell to be mixed in the mixing step are the mesenchymal stem cells having been proliferated in the proliferation step and detached from the medium by a conventionally publicly-known method. The method for detaching the mesenchymal stem cells from the medium encompasses a method employing a cell detachment agent (such as Accutase) which does not contain any component derived from mammals and microorganisms as described above.

Further, the mesenchymal stem cells to be mixed in the mixing step may be mesenchymal stem cells which have been cryopreserved (e.g., at −80° C.) and then thawed, after proliferation in the proliferation step. In a case where cryopreserved mesenchymal stem cells are to be used, the mesenchymal stem cells may be mesenchymal stem cells which are (i) thawed and then cultured in the serum-free medium A until the mesenchymal stem cells reach a pre-confluent state and (ii) subcultured once, after it has been checked in advance that the mesenchymal stem cells has a proliferation ability. Further, in a case where cryopreserved mesenchymal stem cells are to be used, it is preferable to check in advance that the mesenchymal stem cells have a differentiation ability.

In the mixing step, the mesenchymal stem cells in the cell administration solution (i.e., the cartilage-damage treatment agent) are mixed so that the number of the mesenchymal stem cells will be preferably $1 \times 10^5$ cells/mL or more and $1 \times 10^8$ cells/mL or less, more preferably $1 \times 10^6$ cells/mL or more and $5 \times 10^7$ cells/mL or less, still more preferably $5 \times 10^6$ cells/mL or more and $5 \times 10^7$ cells/mL or less, and most preferably $5 \times 10^6$ cells/mL. By mixing the mesenchymal stem cells in a manner such that the number of the mesenchymal stem cells is within the above range, it is possible to favorably promote regeneration of a cartilage when a product cartilage-damage treatment agent is administered to a site of cartilage damage.

<Isotonic Preserving Agent>

Examples of the isotonic preserving agent to be mixed in the mixing step encompass lactated Ringer's solution, but not limited to this. As the lactated Ringer's solution, commercially available lactated Ringer's solution can be used. For example, as the lactated Ringer's solution, SOLULACT (manufactured by Telmo Corporation) can be suitably used. Any one type of such an isotonic preserving agent may be used alone or two or more types of the isotonic preserving agent may be used in combination.

<Cytoprotective Agent>

Examples of the cytoprotective agent to be mixed in the mixing step encompass hyaluronic acid, but not limited to this. It is preferable that an average molecular weight of hyaluronic acid to be used as the cytoprotective agent be preferably 1500000 or more and 3900000 or less. Any one type of the cytoprotective agent may be used alone or two or more types of the cytoprotective agent may be used in combination.

In the mixing step, the cytoprotective agent is mixed so that a concentration of the cytoprotective agent in the cell administration solution (i.e., the cartilage-damage treatment agent) will be preferably more than 0% and 0.5% or less, more preferably 0.005% or more and 0.1% or less, still more preferably 0.01% or more and 0.1% or less, and most preferably 0.01%.

Accordingly, respective amounts of the isotonic preserving agent and the cytoprotective agent to be mixed in the mixing step are determined depending on a concentration of the cytoprotective agent prior to mixing. In other words, in a case where an amount of the cell administration solution to be prepared by mixing the mesenchymal stem cells, the isotonic preserving agent, and the cytoprotective agent is, for example, 1 mL and a concentration of the cytoprotective agent prior to mixing is 1%, 100 μL of the cytoprotective agent and 900 μL of the isotonic preserving agent are mixed in the mixing step so that a concentration of the cytoprotective agent will be 0.1% in the cell administration solution. Meanwhile, in a case where an amount of the cell administration solution to be prepared is, for example, 1 mL and a concentration of the cytoprotective agent prior to mixing is 1%, 10 μL of the cytoprotective agent and 990 μL of the isotonic preserving agent are mixed in the mixing step so that a concentration of the cytoprotective agent will be 0.01% in the cell administration solution.

The inventors of the present application found that a cartilage regeneration ability of the cartilage-damage treatment agent is superior in a case where the cytoprotective agent is contained at a low concentration as described above as compared to a case where the cytoprotective agent is contained at a high concentration. In other words, it is possible to prevent deterioration in function of the mesenchymal stem cells and more favorably promote regeneration of a cartilage by mixing the cytoprotective agent in a manner such that the concentration of the cytoprotective agent becomes within the above range.

Further, the inventors of the present application found that in a case where the concentration of the cytoprotective agent is 0.01% or more and 0.1% or less in a prepared cell administration solution, a decrease in viability of the mesenchymal stem cells due to storage of the cell administration solution is prevented. In other words, when the cytoprotective agent is mixed so that the concentration of the cytoprotective agent will be within the above range, it is possible to provide a cartilage-damage treatment agent which can endure a longer-term storage.

In the mixing step, other component may be mixed, provided that the component causes no change in cartilage regeneration function of the cartilage-damage treatment agent.

The cell administration solution prepared in the mixing step may be stored, for example, at a temperature in a range of 4° C. to 37° C. for a predetermined period, until the cell administration solution is administered to a site of cartilage damage. In a case where the cell administration solution is stored, refrigerated storage (4° C.) is more preferable. In a case where a concentration of the cytoprotective agent is 0.01% or more and 0.1% or less, a cell viability of 60% or more can be maintained even in a case where the cell administration solution is stored at 4° C. for one month or longer. Further, at the concentration of 0.01% or more and 0.1% or less, a cell viability of 70% or more can be maintained for 24 hours even in a case where the cell administration solution is stored at 37° C. In a case where the cell administration solution has been stored for a predetermined period, it is preferable to check that the mesenchymal stem cells have a differentiation ability prior to administration.

(Pre-Proliferation Step)

The method according to the present invention for producing the cartilage-damage treatment agent may further include, before the proliferation step, a pre-proliferation step of pre-proliferating the mesenchymal stem cells in a serum-free medium B containing an FGF, a PDGF, an EGF, at least one phospholipid, and at least one fatty acid.

<Serum-Free Medium B>

The serum-free medium B is different from the serum-free medium A described in the above "Proliferation Step" in that the serum-free medium B does not contain an HGF and a TGF-β. As to components except the HGF and the TGF-β (an FGF, a PDGF, an EGF, at least one phospholipid, and at least one fatty acid) and a basal medium in the medium B, the description for those of the serum-free medium A in the above "Proliferation Step" applies, so that the description thereof is omitted here.

Further, in one embodiment, the serum-free medium B, like the serum-free medium A, preferably contains a lipid antioxidant. Further, the serum-free medium B may further include a surfactant. Further, the serum-free medium B may further contain insulin, transferrin, and selenate. The serum-free medium B may further contain dexamethasone or another glucocorticoid. These components also have already been described in connection with the serum-free medium A in the above "Proliferation Step", so that the description thereof is omitted here.

Note that contents of those components contained in the serum-free medium B may be the same as those of the serum-free medium A or may be different from those of the serum-free medium A, provided that the contents of the components fall within ranges of the contents of the components of the serum-free medium A described in the above "Proliferation Step".

In the pre-proliferation step, the mesenchymal stem cells isolated from animal tissues (such as human tissues) by a conventionally publicly-known method are inoculated into the serum-free medium B, and are cultured until the number of mesenchymal stem cells proliferated reaches the desired number of the mesenchymal stem cells. As a culture condition, preferably, 1 to 500 mg of a tissue slice(s) (containing MSCs) is separated per 1 mL of a medium and the mesenchymal stem cells are inoculated into the medium. As other culture conditions, it is preferable that: a culture temperature be 37° C.±1° C.; a culture time be 3 to 14 days; and the mesenchymal stem cells be under 5% $CO_2$.

The mesenchymal stem cells which are to be subjected to the pre-proliferation step are not particularly limited. However, the mesenchymal stem cells are preferably initial mesenchymal stem cells, i.e., are preferably cells which have never been subcultured after being collected from animal tissues (such as human tissues). As described in Examples (described later), initial mesenchymal stem cells are preliminarily proliferated in the serum-free medium B before the proliferation step is carried out. This makes it possible to remarkably increase the number of the mesenchymal stem cells obtained in the proliferation step.

A method for culturing mesenchymal stem cells in the pre-proliferation step in one embodiment is, for example, as follows: the mesenchymal stem cells are inoculated into the serum-free medium B at an inoculation density of $2 \times 10^5$ cells/$cm^2$; after that, the mesenchymal stem cells are incubated and proliferated for about one week while the serum-free medium B is added every two days in an amount equivalent to 10% of the amount of the culture fluid at the inoculation, until the number of cells reaches 70 to 80% of the number in a confluent state. The mesenchymal stem cells thus preliminarily cultured in the serum-free medium B as described above are subjected to the proliferation step. This makes it possible to efficiently obtain a large number of mesenchymal stem cells whose differentiation ability is maintained.

Further, in order to efficiently proliferate the mesenchymal stem cells in the pre-proliferation step, it is preferable that the pre-proliferation step be carried out in a culture vessel suitable for proliferation of a particular kind of the mesenchymal stem cells to be proliferated in the pre-proliferation step (hereinafter, these mesenchymal stem cells are also referred to as a "pre-proliferation target cells"). As to a method for selecting a culture vessel suitable for pre-proliferation of the proliferation target cells, the description in the above "Proliferation Step" applies, so that the description thereof is omitted here.

In a case where adhesion of the pre-proliferation target cells with respect to the culture vessel is not sufficient, the serum-free medium B may further contain cell adhesion molecules in the pre-proliferation step, as in the proliferation step. The cell adhesion molecules have been described in the above "Proliferation Step", so that the description thereof is omitted here.

As in the proliferation step, the mesenchymal stem cells may be subcultured at least once in the pre-proliferation step. It is possible to improve a culture condition by subculturing the mesenchymal stem cells in the process of the pre-proliferation step. Note that it is preferable that the pre-proliferation step is preferably carried out during a period from primary cell culture (P0) to third passage cell culture (P3). As to a method for subculturing the mesenchymal stem cells in the process of the pre-proliferation step and a subculturing method in a case where the mesenchymal stem cells are to be subjected to the proliferation step after the pre-proliferation step, the description in the above "Proliferation Step" applies, so that the description thereof is omitted here.

Note that in a case where in the pre-proliferation step, adhesion or proliferation of the mesenchymal stem cells is insufficient, autologous serum or allogeneic serum may be added into the medium in the process of culturing so that a concentration of the autologous serum or allogeneic serum will be 1% in the medium. Further, an antibiotic may be added into the medium so that a concentration of the antibiotic may become 1% and then gradually decrease, when the mesenchymal stem cells are cultured in the pre-proliferation step.

According to the method of the present invention as described above for producing the cartilage-damage treatment agent, it is possible to proliferate, even in the serum-free medium, the mesenchymal stem cells at a speed equal to or higher than a speed in a case where the mesenchymal stem cells are cultured in a serum-containing medium. Further, the mesenchymal stem cells thus proliferated maintain a differentiation ability. Accordingly, when the cartilage-damage treatment agent containing such mesenchymal stem cells is administered to a patient, it is possible to realize not only an excellent transplantation treatment because of the mesenchymal stem cells, but also a stable treatment. Further, it is unnecessary to consider a lot difference of the serum, unlike a conventional cell formulation produced by use of serum. This makes it possible to realize a stable cure rate in the transplantation treatment.

2. Cartilage-Damage Treatment Agent

The present invention provides a cartilage-damage treatment agent containing mesenchymal stem cells. The cartilage-damage treatment agent according to the present invention includes mesenchymal stem cells cultured in a serum-free medium A containing an FGF, a PDGF, a TGF-β, an HGF, an EGF, at least one phospholipid and at least one fatty acid; an isotonic preserving agent; and a cytoprotective agent.

(Mesenchymal Stem Cells)

The mesenchymal stem cells contained in the cartilage-damage treatment agent encompasses not only cells isolated from adult tissues of synovial membrane cells, adipose cells, bone marrow, an alveolar bone, a periodontal membrane, and the like but also cells isolated from various cells etc. of placenta, umbilical cord, cord blood, and fetus. The mesenchymal stem cells to be proliferated in the proliferation step are preferably derived from tissues selected from the group consisting of synovial membrane, umbilical cord, cord blood, amnion, bone marrow, and adipose tissues.

The mesenchymal stem cells contained in the cartilage damage treatment agent preferably are cells of a patient himself/herself to whom the cartilage-damage treatment agent is to be administered. Alternatively, the mesenchymal stem cells may be allogeneic cells. Further, the mesenchymal stem cells may be human mesenchymal stem cells or alternatively mesenchymal stem cells derived from non-human animals such as mice, rats, cats, dogs, etc.

It is possible to employ a conventionally publicly-known method as a method for isolating mesenchymal stem cells from tissues. For example, the mesenchymal stem cells can be preferably isolated from tissues by a collagenase method.

The mesenchymal stem cells contained in the cartilage-damage treatment agent are mesenchymal stem cells cultured and proliferated in the above-described serum-free medium A. In other words, the mesenchymal stem cells contained in the cartilage-damage treatment agent are mesenchymal stem cells proliferated in the proliferation step in the above-described method for producing the cartilage-damage treatment agent. Further, the mesenchymal stem cells contained in the cartilage-damage treatment agent may be mesenchymal stem cells which are first cultured and proliferated in the above-described serum-free medium B, and then, further cultured and proliferated in the serum-free medium A. In other words, the mesenchymal stem cells contained in the cartilage-damage treatment agent may be mesenchymal stem cells which are proliferated in the proliferation step after having been proliferated in the pre-proliferation step in the above-described method for producing the cartilage-damage treatment agent.

Further, the mesenchymal stem cells contained in the cartilage-damage treatment agent may be mesenchymal stem cells which have been cryopreserved (e.g., at −80° C.) and then thawed, after culturing in the serum-free medium A and detachment with use of a cell detachment agent from the serum-free medium A. The mesenchymal stem cells contained in the cartilage damage treatment agent may be mesenchymal stem cells which are (i) thawed and then cultured in the serum-free medium A until the mesenchymal stem cells reach a preconfluent state, and (ii) further sub-cultured once.

The number of mesenchymal stem cells contained in the cartilage-damage treatment agent is preferably $1 \times 10^5$ cells/mL or more and $1 \times 10^8$ cells/mL or less, more preferably $1 \times 10^6$ cells/mL or more and $5 \times 10^7$ cells/mL or less, still more preferably $5 \times 10^6$ cells/mL or more and $5 \times 10^7$ cells/mL or less, and most preferably $5 \times 10^6$ cells/mL. By containing the mesenchymal stem cells in the above range, it is possible to favorably promote regeneration of a cartilage when the cartilage-damage treatment agent is administered to a site of cartilage damage.

It is preferable that the mesenchymal stem cells contained in the cartilage-damage treatment agent maintain a differentiation ability. In other words, the mesenchymal stem cells contained in the cartilage-damage treatment agent are undifferentiated and have a differentiation ability to differentiate into adipose cells, bone cells, chondrocytes, and the like cells. Such a cartilage-damage treatment agent is administered to a site of cartilage damage, so that the mesenchymal stem cells maintaining the differentiation ability can be administered to the site of cartilage damage.

(Isotonic Preserving Agent)

Examples of the isotonic preserving agent contained in the cartilage-damage treatment agent encompass lactated Ringer's solution, but not limited to this. As the lactated Ringer's solution, commercially available lactated Ringer's solution can be used. For example, as the lactated Ringer's solution, SOLULACT (manufactured by Telmo Corporation) can be suitably used. The cartilage damage treatment agent may contain, as the isotonic preserving agent, any one type of such an isotonic preserving agent alone or two or more types of the isotonic preserving agent in combination.

(Cytoprotective Agent)

Examples of the cytoprotective agent contained in the cartilage-damage treatment agent encompass hyaluronic acid, but not limited to this. It is preferable that an average molecular weight of hyaluronic acid to be used as the cytoprotective agent be preferably 1500000 or more and 3900000 or less. The cartilage-damage treatment agent may contain as the cytoprotective agent any one type of the cytoprotective agent alone or two or more types of the cytoprotective agent in combination.

A concentration of the cytoprotective agent contained in the cartilage-damage treatment agent is preferably more than 0% and 0.5% or less, more preferably 0.005% or more and 0.1% or less, still more preferably 0.01% or more and 0.1% or less, and most preferably 0.01%.

Respective amounts of the isotonic preserving agent and the cytoprotective agent to be contained in the cartilage-damage treatment agent are determined depending on a concentration of the cytoprotective agent. In other words, in a case where a total amount of the cartilage-damage treatment agent is, for example, 1 mL and a concentration of the cytoprotective agent prior to mixing of the cytoprotective agent into the cartilage-damage treatment agent is 1%, the cartilage-damage treatment agent contains 100 μL of the cytoprotective agent and 900 μL of the isotonic preserving agent if a concentration of the cytoprotective agent is 0.1% in the cartilage-damage treatment agent. On the other hand, in a case where a total amount of the cartilage-damage treatment agent is, for example, 1 mL and a concentration of the cytoprotective agent prior to mixing of the cytoprotective agent into the cartilage-damage treatment agent is 1%, the cartilage-damage treatment agent contains 10 μL of the cytoprotective agent and 990 μL of the isotonic preserving agent if a concentration of the cytoprotective agent is 0.01% in the cartilage-damage treatment agent.

The inventors of the present application found that a cartilage regeneration ability of the cartilage-damage treatment agent is superior in a case where the cytoprotective agent is contained at a low concentration as described above as compared to a case where the cytoprotective agent is contained at a high concentration. In other words, it is possible to prevent deterioration in function of the mesenchymal stem cells and more favorably promote regeneration of a cartilage, by containing the cytoprotective agent at a concentration in the above range.

Further, the inventors of the present application found that in a case where the concentration of the cytoprotective agent is 0.01% or more and 0.1% or less, a decrease in viability of the mesenchymal stem cells due to storage of the cell administration solution is prevented. In other words, the cartilage-damage treatment agent can endure a longer-term storage by containing the cytoprotective agent at a concentration in the above range.

The cartilage-damage treatment agent may contain other component, provided that the component causes no change in cartilage regeneration function of the cartilage-damage treatment agent.

(Applications of Cartilage-Damage Treatment Agent)

The cartilage-damage treatment agent according to the present invention is used to regenerate a cartilage by administration of the cartilage damage treatment agent to a site of cartilage damage. Further, thought the cartilage-damage treatment agent may be administered to a site of full-thickness damage at which site at least a part of a bone is exposed due to damage to a cartilage covering the bone, it is preferable that the cartilage-damage treatment agent be administered to a site of partial damage at which site a cartilage is partially damaged to an extent that a bone is not exposed or to a site of half-thickness damage at which site about half a thickness of a cartilage is damaged. Further, it is also effective to administer the cartilage-damage treatment agent to a site where a degenerated portion of a cartilage is removed.

The cartilage-damage treatment agent can be administered to a site of articular cartilage damage. For example, the cartilage damage treatment agent can be administered to a site of knee articular cartilage damage, ankle articular cartilage damage, shoulder articular cartilage damage, or the like damage. Further, the cartilage-damage treatment agent can also be administered to a site of intervertebral disc damage or intervertebral disc degeneration, so that the cartilage-damage treatment agent can be used for regeneration of intervertebral disc and/or improvement of nucleus pulposus degeneration.

An amount of the cartilage-damage treatment agent according to the present invention to be administered at a time to a site of cartilage damage is preferably 0.5 mL or more and 10 mL or less, more preferably 1 mL or more and 5 mL or less, and most preferably 1 mL or more and 3 mL or less. This makes it possible to more effectively regenerate a cartilage at a site of cartilage damage.

Further, the cartilage-damage treatment agent according to the present invention is administered to each treatment target site preferably one time or more and ten times or less, more preferably one time and more and five times and less, and most preferably one time or more and three times or less. This makes it possible more effectively regenerate a cartilage at a site of cartilage damage.

Further, in a case where the cartilage-damage treatment agent according to the present invention is to be administered two or more times to each treatment target site, the cartilage-damage treatment agent is administered preferably every 3 to 28 days, more preferably every 3 to 21 days, and most preferably every 3 to 7 days. This makes it possible more effectively regenerate a cartilage at a site of cartilage damage.

Further, a method for administrating the cartilage-damage treatment agent according to the present invention is preferably a method in which the cartilage-damage treatment agent is administered into a joint cavity by a syringe or the like. Further, in order to appropriately administer the cartilage-damage treatment agent into a joint cavity, the cartilage-damage treatment agent may be administered while a position to which the cartilage-damage treatment agent is to be administered is being checked under an arthroscope. Furthermore, the cartilage-damage treatment agent may be administered, after a site of cartilage damage is scraped so that a site of damage may be cleaned.

The cartilage-damage treatment agent according to the present invention makes it possible to promote regeneration of a cartilage at a site of cartilage damage by direct administration of the cartilage-damage treatment agent to the site of cartilage damage. The inventors of the present application found that: a function of mesenchymal stem cells as well as an anti-inflammatory effect and an immunological tolerance effect that the mesenchymal stem cells essentially have are sufficiently protected by the cytoprotective agent by administrating, to a site of cartilage damage, a cartilage-damage treatment agent containing the cytoprotective agent and the mesenchymal stem cells which have been cultured in a serum-free medium while a differentiation ability of the mesenchymal stem cells is maintained, and as a result, (i) the mesenchymal stem cell can release in a favorable manner cytokines which contribute to regeneration of a cartilage and (ii) homing of the mesenchymal stem cells toward a site of cartilage damage occurs in a favorable manner. Consequently, the inventors have accomplished the present invention.

The mesenchymal stem cells contained in the cartilage-damage treatment agent according to the present invention are more favorably protected by the cytoprotective agent. Accordingly, as illustrated in FIG. 1, the mesenchymal stem cells stay alive for a long term at a site of cartilage damage to which site the cartilage-damage treatment agent is administered. This allows the mesenchymal stem cells at the site of cartilage damage to continuously release cytokines which contribute to regeneration of a cartilage. In addition, favorable homing of the mesenchymal stem cells toward the site of cartilage damage occurs. FIG. 1 is a schematic view illustrating a mechanism of the present invention.

Then, the cytokines released from the mesenchymal stem cells contained in the cartilage-damage treatment agent stimulate fibroblasts, vascular endothelial cells, and the like to proliferate at the site of cartilage damage. This initiates angiogenesis at the site of cartilage damage, so that fibroblasts and related cells accumulate at the site of cartilage damage and thereby extracellular matrices are freshly formed and deposited, continuously. Further, the mesenchymal stem cells having homed to the site of cartilage damage adhere to the site, then proliferate and differentiate, and consequently regenerate a cartilage tissue.

As described above, in the cartilage-damage treatment agent according to the present invention, the mesenchymal stem cells themselves contained in the cartilage-damage treatment agent per se differentiate into chondrocytes and regenerate a cartilage tissue at a site of cartilage damage to which site the cartilage-damage treatment agent is administered. The mesenchymal stem cells also stay alive in an undifferentiated state at the site of cartilage damage for a long term and continue releasing cytokines which contribute to regeneration of a cartilage, so that regeneration of the cartilage is promoted. Of course, the anti-inflammatory effect and the immunological tolerance effect that the mesenchymal stem cells have allow allogeneic transplantation.

Further, the cartilage-damage treatment agent according to the present invention contains the isotonic preserving agent. This makes it possible to prevent deterioration in viability of the mesenchymal stem cells in the cartilage-damage treatment agent, and to store the cartilage-damage treatment agent for a long term. In other words, the cartilage-damage treatment agent according to the present invention can be prepared in advance and thus prepared cartilage-damage treatment agent can be administered to a patient when necessary. This significantly reduces the burden on the patient.

In this way, the cartilage-damage treatment agent according to the present invention makes it possible to regenerate a cartilage only by administration of the cartilage-damage treatment agent to a site of cartilage damage by use of a syringe or the like. Therefore, tissues other than a damaged cartilage tissue may not be unnecessarily damaged.

Further, the cartilage-damage treatment agent according to the present invention can be used not only for treatment by autologous transplantation but also for treatment by allogenic transplantation in which a non-self tissue or cell is transplanted (a donor and a recipient are different). The cartilage-damage treatment agent can also be preferably used not only for allotransplantation (allogeneic transplantation) by use of human tissues or human cells but also for xenotransplantation (heterotransplantation) by use of animal tissues (except human tissues) or animal cells (except human cells). Accordingly, it is not necessary to obtain cells from a patient himself/herself. This reduces the burden on the patient. Further, it also becomes possible to timely provide a cartilage-damage treatment agent for many patients. In addition, patients can be treated by one operation.

Further, the cartilage-damage treatment agent according to the present invention makes it possible to regenerate a cartilage by one-time administration. Accordingly, it is not necessary to repeat treatment. This reduces physical, psychological, and economical burdens on patients. Further, the cartilage-damage treatment agent according to the present invention makes it possible to reliably regenerate a cartilage in a short term.

Further, the cartilage-damage treatment agent according to the present invention contains serum-free cultured mesenchymal stem cells. Accordingly, there is no risk of administering, into a patient body, unknown pathogens (viruses, pathogenetic prions, etc.) mixed in serum. Further, serum is very expensive. In addition, serum tends to cause variation in cell proliferation effect, since components of serum vary in each lot because the serum is a natural product. However, the present invention makes no use of serum and therefore, the above problems never occur. Furthermore, it is unnecessary to purify cultured mesenchymal stem cells for the purpose of removing serum-derived proteins and the like from the cultured mesenchymal stem cells. This makes operations more efficient.

Further, the cartilage-damage treatment agent according to the present invention is scaffold-free. Accordingly, unlike conventional cultured chondrocyte transplantation, it is not necessary to obtain a periosteum from a healthy region and cover a transplanted region. Therefore, there is no risk of onset of an adverse event caused by obtaining periosteum.

Note that the scope of the present invention encompasses a cartilage damage treatment method with use of the cartilage-damage treatment agent according to the present invention and a cartilage tissue regeneration method with use of the cartilage-damage treatment agent according to the present invention. The cartilage damage treatment method and the cartilage tissue regeneration method encompass the step of administering, to an administration site of a patient as described above, the cartilage-damage treatment agent according to the present invention in the above-described dose, the above-described number of times of administration, and at the above-described time for administration.

3. Serum-Free Additive for Medium for Producing Cartilage-Damage Treatment Agent The present invention provides a serum-free additive for a medium for producing a cartilage-damage treatment agent containing mesenchymal stem cells. The additive for a medium according to the present invention contains an FGF, a PDGF, a TGF-β, an HGF, an EGF, at least one phospholipid and at least one fatty acid. The additive for a medium according to the present invention is added to a conventionally publicly-known basal medium and a resultant medium can be used as a serum-free medium (serum-free medium A) for producing the cartilage-damage treatment agent containing mesenchymal stem cells.

Examples of the phospholipid contained in the additive for a medium according to the present invention encompass phosphatidic acid, lysophosphatidic acid, phosphatidylinositol, phosphatidyl serine, phosphatidyl ethanolamine, phosphatidyl choline, and phosphatidyl glycerol. The additive for a medium according to the present invention may contain any one of these phospholipids alone, or two or more of the phospholipids in combination. In one embodiment, the additive for a medium according to the present invention contains phosphatidic acid and phosphatidyl choline in combination. Further, those phospholipids may be derived from animals or plants.

Examples of the fatty acid contained in the additive for a medium according to the present invention encompass linoleic acid, oleic acid, linolenic acid, arachidonic acid, myristic acid, palmitoleic acid, palmitic acid, and stearic acid. The additive for a medium according to the present invention may contain any one of those fatty acids alone or two or more types of the fatty acids in combination. Further, the additive for a medium according to the present invention may contain not only the fatty acid(s) but also cholesterol.

The term "FGF" as used herein means a growth factor selected from a fibroblast growth factor (FGF) family, and is preferably FGF-2 (bFGF). However, other FGFs of the FGF family, such as FGF-1, may also be selected.

The term "PDGF" as used herein means a growth factor selected from a platelet derived growth factor (PDGF) family, and is preferably PDGF-BB or PDGF-AB.

The term "TGF-β" as used herein means a growth factor selected from a transforming growth factor-β (TGF-β) family, and is preferably TGF-β3. However, other TGF-βs of the TGF-β family may also be selected.

The term "HGF" as used herein means a growth factor selected from a hepatocyte growth factor family, and the term "EGF" as used herein means a growth factor selected from an epidermal growth factor (EGF) family.

In one embodiment, the additive for a medium may further contain at least two factors selected from the group consisting of a connective tissue growth factor (CTGF), a vascular endothelial growth factor (VEGF), and an ascorbic acid compound.

The term "ascorbic acid compound" as used herein means ascorbic acid (vitamin C), ascorbic acid-2-phosphate, or a compound similar to these ascorbic acids.

Note that the growth factors contained in the additive for a medium according to the present invention may be naturally-occurring ones or may be ones produced by gene modification.

In one embodiment, the additive for a medium according to the present invention preferably contains a lipid antioxidant. The lipid antioxidant contained in the additive for a medium according to the present invention may be DL-α-tocopherol acetate (vitamin E) in one embodiment. The additive for a medium according to the present invention may further contain a surfactant. The surfactant contained in the additive for a medium according to the present invention may be Pluronic F-68 or Tween 80 in one embodiment.

The additive for a medium according to the present invention may further contain insulin, transferrin, and selenate. The term "insulin" as used herein may mean an insulin-like growth factor, and may be derived from a natural cell or may be produced by gene modification. The additive for a medium according to the present invention may further contain dexamethasone, or another glucocorticoid.

4. Serum-Free Culturing Medium for Producing Cartilage-Damage Treatment Agent The present invention provides a serum-free culturing medium for producing a cartilage-damage treatment agent containing mesenchymal stem cells. The culturing medium according to the present invention contains an FGF, a PDGF, a TGF-β, an HGF, an EGF, at least one phospholipid, and at least one fatty acid. The culturing medium according to the present invention can be used as a serum-free medium (serum-free medium A) for producing a cartilage-damage treatment agent containing mesenchymal stem cells.

The culturing medium according to the present invention contains an FGF, a PDGF, a TGF-β, an HGF, an EGF, at least one phospholipid, and at least one fatty acid, and these components may be simultaneously added to the basal medium, or may be separately added. That is, it can be said that the culturing medium according to the present invention only needs to contain the components contained in the additive for a medium as described above or components contained in a kit for an additive for a medium as described later.

A basal medium for constituting the culturing medium according to the present invention is not particularly limited, provided that the basal medium is a well-known medium for animal cells in this field. A preferable examples of the basal medium encompass a Ham's F12 medium, a DMEM medium, an RPMI-1640 medium, and an MCDB medium. Such basal mediums each may be used alone, or two or more of such basal mediums may be used in combination. A basal medium for constituting the medium according to the present invention in one embodiment is preferably a medium in which an MCDB medium and a DMEM medium are mixed at a ratio of 1:1.

5. Culture Method for Producing Cartilage-Damage Treatment Agent

The present invention provides a culture method for producing a cartilage-damage treatment agent containing mesenchymal stem cells. The culture method according to the present invention includes the step (culture step A) of culturing the mesenchymal stem cells in the serum-free medium (serum-free medium A) containing an FGF, a PDGF, a TGF-β, an HGF, an EGF, at least one phospholipid, and at least one fatty acid. In the culture method according to the present invention, the serum-free culturing medium can be used in order to culture the mesenchymal stem cells.

The culture method according to the present invention may further include, before the culture step A, the step (culture step B) of culturing mesenchymal stem cells in the serum-free medium B containing an FGF, a PDGF, an EGF, at least one phospholipid, and at least one fatty acid.

Note that the culture step A and the culture step B correspond to the proliferation step and the pre-proliferation step, respectively, in the method for producing a cell formulation containing mesenchymal stem cells according to the present invention. Accordingly, the description of the proliferation step and the pre-proliferation step in the above "Method for Producing Cartilage-Damage Treatment Agent" in the present Specification can be also read as the descriptions of the culture step A and the culture step B, respectively.

In one embodiment, the culture method according to the present invention may include the step of simultaneously adding an FGF, a PDGF, a TGF-β, an HGF, an EGF, at least one phospholipid, and at least one fatty acid to the basal medium. In one embodiment, the culture method according to the present invention may include the step of simultaneously adding an FGF, a PDGF, an EGF, at least one phospholipid, and at least one fatty acid to the basal medium. The basal medium is not particularly limited, provided that the basal medium is a medium for animal cells, which is well-known in this field.

6. Kit for Producing Cartilage-Damage Treatment Agent

The present invention provides a kit for producing a cartilage-damage treatment agent containing mesenchymal stem cells. The kit according to the present invention contains an FGF, a PDGF, a TGF-β, an HGF, an EGF, at least one phospholipid and at least one fatty acid.

The kit according to the present invention may contain an FGF, a PDGF, a TGF-β, an HGF, an EGF, at least one phospholipid, and at least one fatty acid in one vessel, or separately contain these components. The kit according to the present invention may further contain cell adhesion molecules. The cell adhesion molecules have been described in the proliferation step in the above "Method for Producing Cartilage-Damage Treatment Agent" in the present Specification, so that the description thereof is omitted here.

The kit according to the present invention can be used as a serum-free medium (serum-free medium A) for producing the cartilage-damage treatment agent containing mesenchymal stem cells, when the kit is added to a conventionally publicly-known basal medium.

The term "composition" as used herein means a form containing various main components in one material, and the term "kit" as used herein means a form containing at least one of the various main components in a separate material. Therefore, it is easily understood that the growth factors, the at least one phospholipid, and the at least one fatty acid included in the kit according to the present invention are the same as those described above for the additive for a medium.

The kit according to the present invention is a kit for producing the cartilage-damage treatment agent containing mesenchymal stem cells, and includes at least the additive for a medium (additive A for a medium) according to the present invention. Further, the kit according to the present invention may further include an additive B for a medium which additive B contains an FGF, a PDGF, an EGF, at least one phospholipid, and at least one fatty acid. Note that the above description of the serum-free medium B can be also read as the description for the additive B for a medium.

Further, the kit according to the present invention may contain at least one of an isotonic preserving agent, a cytoprotective agent, a culture vessel, instructions for use and the like. The isotonic preserving agent, the cytoprotective agent, and the culture vessel are the same as those described in the above "Method for Producing Cartilage-Damage Treatment Agent" in the present Specification, and therefore, descriptions thereof are omitted here. The instructions for use records, for example, the contents of the method of the present invention for producing the cartilage-damage treatment agent as described in the above "Method for Producing Cartilage-Damage Treatment Agent".

7. Overview

A method according to the present invention for producing a cartilage-damage treatment agent, includes the steps of: (i) proliferating mesenchymal stem cells in a serum-free medium A containing an FGF, a PDGF, a TGF-β, an HGF, an EGF, at least one phospholipid and at least one fatty acid; and (ii) mixing the mesenchymal stem cells thus proliferated in the step (i), an isotonic preserving agent, and a cytoprotective agent.

Preferably, the method according to the present invention is arranged such that in the step (ii), the mesenchymal stem cells are mixed so that the number of the mesenchymal stem cells is $1 \times 10^5$ cells/mL or more and $1 \times 10^8$ cells/mL or less.

Preferably, the method according to the present invention is arranged such that in the step (ii), the cytoprotective agent is mixed so that a concentration of the cytoprotective agent is more than 0% and 0.5% or less.

More preferably, the method according to the present invention is arranged such that in the step (ii), the cytoprotective agent is mixed so that a concentration of the cytoprotective agent is 0.01% or more and 0.1% or less.

Preferably, the method according to the present invention is arranged such that the mesenchymal stem cells are derived from a tissue selected from the group consisting of synovial membrane, umbilical cord, cord blood, amnion, bone marrow, and an adipose tissue.

Preferably, the method according to the present invention is arranged such that in the step (i), the mesenchymal stem cells are proliferated while a differentiation ability of the mesenchymal stem cells is maintained.

Preferably, the method according to the present invention is arranged to further include the step of pre-proliferating the mesenchymal stem cells in a serum-free medium B containing an FGF, a PDGF, an EGF, at least one phospholipid, and at least one fatty acid, prior to the step (i).

A cartilage-damage treatment agent according to the present invention includes: mesenchymal stem cells cultured in a serum-free medium A containing an FGF, a PDGF, a TGF-β, an HGF, an EGF, at least one phospholipid and at least one fatty acid; an isotonic preserving agent; and a cytoprotective agent.

Preferably, the cartilage-damage treatment agent according to the present invention is arranged such that the number of the mesenchymal stem cells is $1 \times 10^5$ cells/mL or more and $1 \times 10^8$ cells/mL or less.

Preferably, the cartilage-damage treatment agent according to the present invention is arranged such that a concentration of the cytoprotective agent is more than 0% and 0.5% or less.

More preferably, the cartilage-damage treatment agent according to the present invention is arranged such that a concentration of the cytoprotective agent is 0.01% or more and 0.1% or less.

Preferably, the cartilage-damage treatment agent according to the present invention is arranged such that the mesenchymal stem cells maintain a differentiation ability.

Preferably, the cartilage-damage treatment agent according to the present invention is administered to a site of cartilage damage at which site part of a cartilage is damaged.

Preferably, the cartilage-damage treatment agent according to the present invention is administered two or more times to the site of cartilage damage.

An additive for a medium according to the present invention is a serum-free additive for a medium for producing a cartilage-damage treatment agent, the serum-free additive containing an FGF, a PDGF, a TGF-β, an HGF, an EGF, at least one phospholipid, and at least one fatty acid.

A culturing medium according to the present invention is a serum-free culturing medium for producing a cartilage-damage treatment agent, the serum-free culturing medium containing the serum-free additive for a medium according to the present invention.

A culture method according to the present invention is a culture method for producing a cartilage-damage treatment agent, the culture method including the step of culturing mesenchymal stem cells in the serum-free culturing medium according to the present invention.

A kit according to the present invention is a kit including at least the serum-free additive for a medium according to the present invention.

The present invention is not limited to the embodiments, but can be altered by a skilled person in the art within the scope of the claims. An embodiment derived from a proper combination of technical means each disclosed in a different embodiment is also encompassed in the technical scope of the present invention.

EXAMPLES

I. Experiments on Cartilage Regeneration (1. Cell Culturing)

A cartilage defect model of a dog was prepared with use of a temporomandibular joint arthroscope whose diameter was 2.0 mm, by causing a half-thickness defect of a cartilage of a knee joint of a healthy adult beagle dog (Kitayama Labes Co., Ltd., age in months: 11 months old, sex: male). Then, a synovial membrane tissue was invasively obtained from another knee joint which was different from the knee joint whose cartilage had the half-thickness defect. Further, thus obtained synovial membrane tissue was immersed in physiological saline solution to which antibiotics (penicillin-streptomycin, concentration: 1%, produced by Sigma-Aldrich Co. LLC.) in a 50 mL tube were added. Subsequently, the synovial membrane tissue was transported to a laboratory. Thus transported tissue was shredded with scissors, treated with collagenase, and then filtrated with a filter. Then, cells from the tissue were inoculated at a uniform cell density into a culture vessel containing a medium 2 (STK1 (registered trademark)) which is a serum-free medium B obtained by removing an HGF and a TGF-β from a medium 1 (STK2 (registered trademark)) that is a serum-free medium A shown in Table 1 below. Then, the cells were cultured in a carbon dioxide gas incubator inside which the temperature was kept at 37° C. (air: 95% and carbon dioxide: 5%).

On the fourth day from the start of culturing (passage 0), cells were collected by treatment with Accutase (Innovative Cell Technologies, Inc.). Further, thus collected cells were inoculated again at a uniform cell density into a culture vessel containing the medium 1 that is the serum-free medium A as shown in Table 1 below. Then, the cells were subcultured.

(STK3 (registered trademark)), and cultured. After 7 days and 21 days from the start of culturing, the cells were stained with alizarin red S (Nacalai Tesque, Inc.: 01303-52). Thereby, it was checked whether or not osteoblast differentiation of the cells was induced. The cells in the medium after 21 days from the start of culturing were stained more than the medium after 7 days from the start of culturing. Accordingly, it was clear that the cells were induced into osteoblasts.

<Adipocyte Differentiation Ability>

The cells were cultured, in the medium 2 and collected when the cells became confluent. Then, thus collected cells were inoculated into an adipocyte differentiation medium (DMEM (Sigma: D5796), FBS (Hyclone), penicillin-streptomycin (Sigma: P0781), insulin (Wako: 093-06471), dexamethasone (Sigma: D1756), indomethacin (Wako: 097-02471), and 3-isobutyl-1-methylxanthine (Calbiochem: 410957)), and cultured. Then, the cells were cultured while an adipocyte-differentiation-inductive medium and an adipocyte-differentiation maintaining medium (MEM (sigma: D5796), FBS (Hyclone), penicillin-streptomycin (Sigma: P0781), insulin (Wako: 093-06471)) were alternately replaced by new ones every three days. After 7 days and 21

TABLE 1

| | Source | Effective concentration |
|---|---|---|
| Basal Medium | | |
| DMEM/MCDB201 | Sigma: D6046/M6770 | 1:1 |
| Supplement A (Basic Factor) | | |
| (human recombinant) Basic fibroblast growth factor (bFGF) | Pepro Tech: 100-18B | 0.1~100 ng/ml |
| Dexamethasone (Dex) | Sigma: D1756 | $10^{-6}$~$10^{-10}$M |
| (human recombinant) Insulin | Wako: 090-03446 | 0.5~50 µg/ml |
| Transferrin | Sigma: T0665 | 0.5~50 µg/ml |
| Selenous acid | Sigma: 21,117-8 | 0.1~50 ng/ml |
| Bovine serum albumin (BSA) | Sigma: A8806 | 0.1~50 mg/ml |
| Supplement B-1 (Basic lipid 1) | | |
| Chemically defined lipid concentrate (CD) | Gibco: 11905-031 | 1/1000~1/10 |
| (concentration of undiluted solution: Arachidonic Acid 2.0 µg/ml, Cholesterol 220.00 µg/ml, DL-α-Tocopherol-Acetate 70.00 µg/ml, Linoleic Acid 540.00 µg/ml, Linolenic Acid 10.00 µg/ml, Myristic Acid 10.00 µg/ml, Oleic Acid 10.00 µg/ml, Palmitoleic Acid 10.0 µg/ml, Palmitic Acid 10.0 µg/ml, Stearic Acid 10.00 µg/ml) | | |
| Supplement B-2 (Basic lipid 2) | | |
| Lecithin from Soybean (LS) | Waco: 120-00832 | 0.5~50 µg/ml |
| cholesterol lipid concentrate (chol) | Gibco: 12531-018 | 0.1~30 µg/ml |
| (+α)-Tocopherol-Acetate (VE) | Sigma: T1157 | 0.1~50 µg/ml |
| Supplement C | | |
| (human recombinant) Hepatocyte growth factor (HGF) | Sigma: H1404 | 0.1~50 ng/ml |
| (human recombinant) Transforming growth factor-$\beta_3$ (TGF-$\beta_3$) | Pepro Tech: 100-36 | 0.5~100 ng/ml |
| (human recombinant) Platelet derived growth factor (PDGF-BB) | Waco: 160-19741 | 0.5~100 ng/ml |
| Others | | |
| (human recombinant) Epidermal growth factor (EGF) | Waco: 050-07141 | 0.5~200 ng/ml |
| Ascorbic acid (VC) | Sigma: A0960 | 0.5~200 µg/ml |
| Phosphatidylcholine (PC) | Wako: 163-21181 | 0.5~100 µg/ml |
| Phosphatidic acid sodium salt (PA) | Sigma: P9511 | 0.5~100 µg/ml |
| (human recombinant) Vascular Endothelial Growth Factor (VEGF) | Sigma: V3388 | 0.5~100 ng/ml |
| (human recombinant) Connective Tissue Growth Factor (CTGF) | Wako: 036-19471 | 0.1~20 µg/ml |

On the ninth day of culturing, it was confirmed that the cells had become confluent. Then, the cells were treated with Accutase and collected, and further cryopreserved at −80° C.

(2. Multipotency Test)

It was checked whether the cells cultured in the above "1. Cell Culturing" maintained a differentiation ability.

<Osteoblast Differentiation Ability>

The cells were cultured in the medium 2, and collected when the cells became confluent. Then, thus collected cells were inoculated into an osteoblast differentiation medium days from the start of culturing, the cells were stained with Oil Red O (WAKO: 154-02072) and whether or not adipocyte differentiation of the cells was induced was checked. The cells in the medium after 21 days from the start of culturing were stained more than the medium after 7 days from the start of culturing. Accordingly, it was clear that the cells were induced into adipose cells.

<Chondrocyte Differentiation Ability>

The cells were cultured in the medium 2, and collected when the cells became confluent. Then, thus collected cells were three-dimensionally cultured in a chondrocyte differentiation medium (αMEM (Sigma: M4526), penicillin-streptomycin (Sigma: P0781), glutaMAX (L-glutamine) (Life Technologies Corporation: 35050-061), dexamethasone (Sigma: D1756), ascorbic acid-2-phosphate (Sigma: A8960), D-glucose (Sigma: G8769), pyruvic acid (Sigma: 28-4020-2), ITS (insulin, transferrin, selenious acid) (Life Technologies Corporation: 41400-045), linoleic acid (Sigma: L5900), BSA (WAKO: 017-15146), and TGF-b3 (peprotec: 100-36E)).

Figure 25:
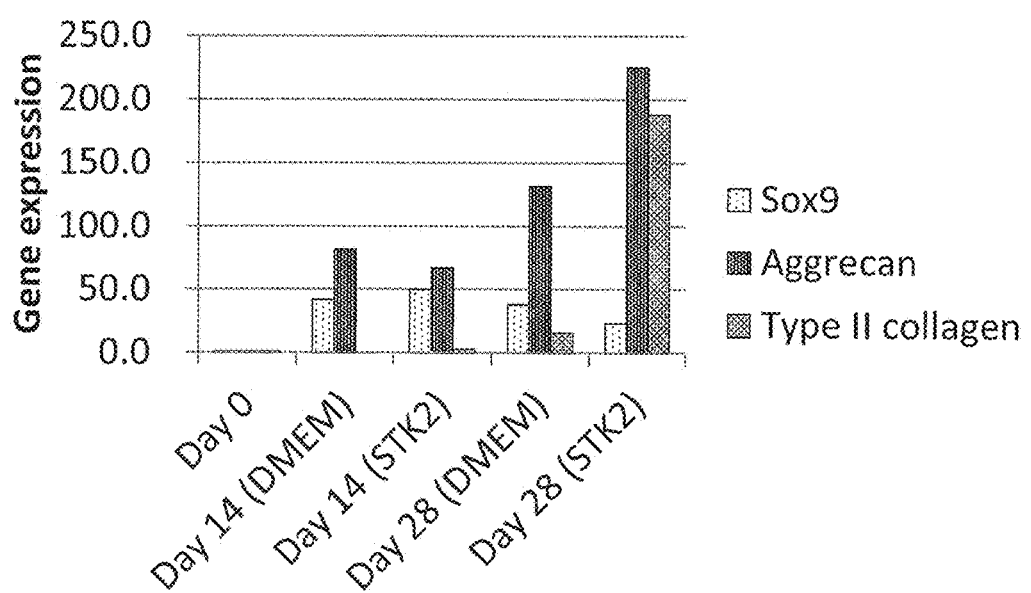
FIG. 25 is a graph showing expression levels of chondrocyte-specific genes (type II collagen, aggrecan, and sox9) of MSCs cultured in a chondrocyte differentiation medium.

In order to check whether differentiation of the cells into chondrocytes was induced, the cells cultured in the chondrocyte differentiation medium were inoculated and cultured in each of the medium 1 (STK2) and the basal medium (DMEM). After 14 days and 28 days from the start of culturing, respective expression levels of chondrocyte-specific genes (type II collagen, aggrecan, and sox9) were measured by real-time PCR. FIG. 25 shows measurement results. FIG. 25 is a graph showing the expression levels of chondrocyte-specific genes (type II collagen, aggrecan, and sox9) of MSCs cultured in the chondrocyte differentiation medium. As shown in FIG. 25, each of all the genes was found to be expressed at a high level. Accordingly, it was clear that the cells were induced into chondrocytes.

(3. Intra-Articular Administration (Single Administration))

<Method>

It was checked in advance that cryopreserved cells had a proliferation ability. Then, culturing was started on the day obtained by back calculation from an administration day. First, the cryopreserved cells were thawed, and then cultured in the STK2 medium until the cells became preconfluent. Then, the cells were subcultured once. Thus subcultured cells were collected on the administration day or a day before the administration day. Then, the number of cells were adjusted, and mixed with hyaluronic acid (SUVENYL (registered trademark), produced by Chugai Pharmaceutical Co., Ltd.) and SOLULACT (lactated Ringer's solution) (manufactured by Telmo Corporation), so that a cell administration solution was prepared.

Thus prepared cell administration solution was transported to an animal experimentation facility (refrigerated storage for 5 to 21 hours) and was put into a syringe. Then, a single administration of this cell administration solution was carried out into the joint (a site of the half-thickness defect of the cartilage of the knee joint) of the cartilage defect model of the dog prepared in the above "1. Cell Culturing".

As a result of measurement of a cell viability in the cell administration solution after the administration, the cells having undergone the refrigerated storage for 21 hours or less maintained a cell viability of 85% or higher, regardless of the number of cells and a hyaluronic acid concentration. Accordingly, it was confirmed that an intra-articular administration had been normally carried out.

<Results>

In order to find out the optimum number of MSCs to be administered and an optimum hyaluronic acid concentration for regeneration of a site of articular cartilage damage, the intra-articular administration as described in the above "3. Intra-articular Administration (Single Administration)" was carried out with use of each of cell administration solutions of various numbers of cells and various hyaluronic acid concentrations.

Then, after 12 weeks from the administration of the cell administration solutions, the site of the half-thickness defect of the cartilage was observed and slices of the site were prepared. Thus prepared slices were subjected to various stainings such as hematoxylin and eosin staining, toluidine blue staining, safranin O staining, and type II collagen staining. Then, a state of repair at the site of the defect was evaluated by microscope observation.

Figure 2:
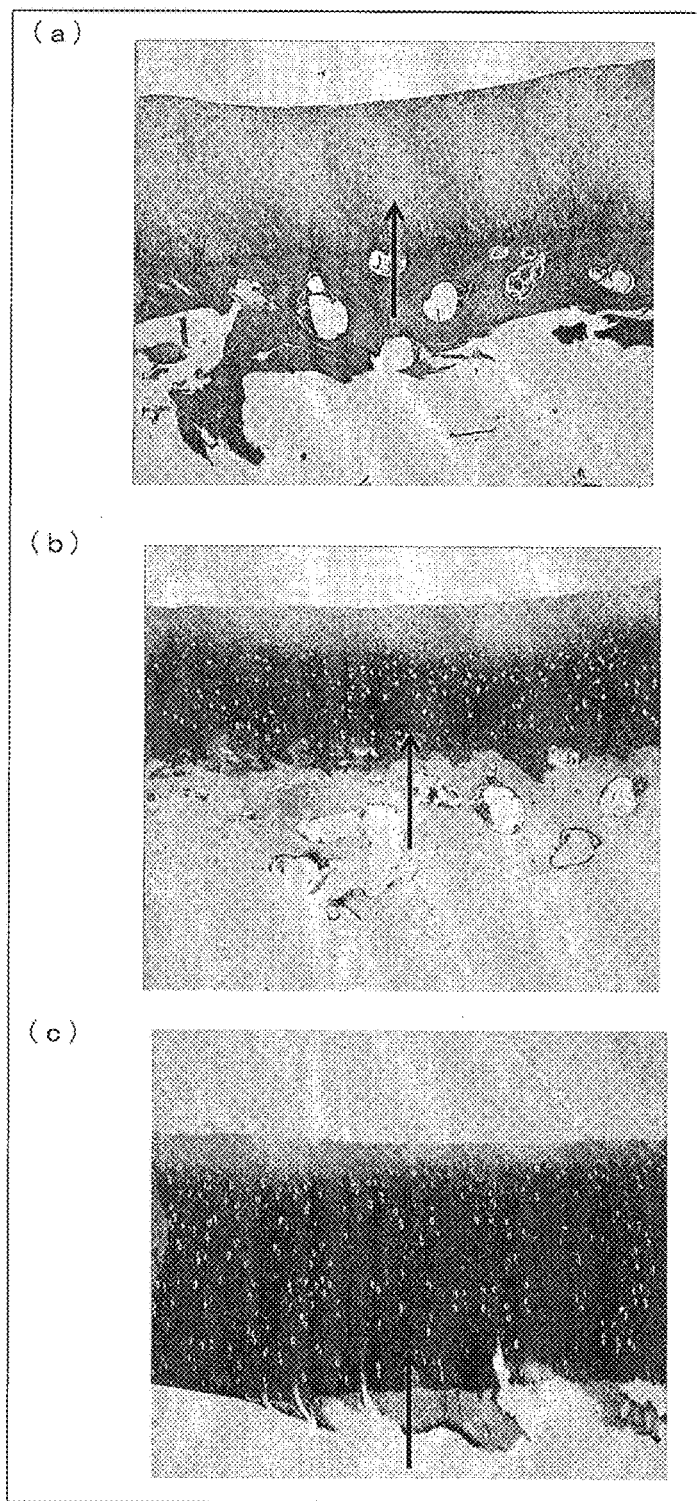
FIG. 2 is a diagram showing microscopic images of a stained healthy cartilage. (a) of FIG. 2 shows a hematoxylin and eosin staining image. (b) of FIG. 2 shows a toluidine blue staining image. (c) of FIG. 2 shows a safranin O staining image.

FIG. 2 shows a microscopic image of a stained healthy hyaline cartilage without any damage in an articular cartilage. (a) of FIG. 2 shows a hematoxylin and eosin staining image. (b) of FIG. 2 shows a toluidine blue staining image. (c) of FIG. 2 shows a safranin O staining image. In FIG. 2, a cartilage matrix was indicated by arrows. The cartilage matrix is stained pale pink by the hematoxylin and eosin staining, stained dark blue by the toluidine blue staining, and stained dark red by the safranin O staining. In drawings, such stained states are shown by gray scale.

Next, FIGS. 3 through 16 show typical microscopic images in cases where the cell administration solutions of various component concentrations each were administered to the site of the half-thickness defect of the cartilage in the above "3. Intra-articular Administration (Single Administration)". Further, the site of the half-thickness defect of the cartilage was evaluated, as macroscopic evaluation, by use of Macroscopic scales of ICRS (International Cartilage Repair Society). Meanwhile, the site of the half-thickness defect of the cartilage was evaluated, as histological evaluation, by use of modified O'Driscoll histological grading scales. Table 2 shows evaluation indices of ICRS Macroscopic scales. Table 3 shows evaluation indices of modified O'Driscoll histological grading scales.

TABLE 2

| Cartilage repair assessment ICRS | Points |
|---|---|
| Degree of defect repair | |
| In level with surrounding cartilage | 4 |
| 75% repair of defect depth | 3 |
| 50% repair of defect depth | 2 |
| 25% repair of defect depth | 1 |
| 0% repair of defect depth | 0 |
| Integration to border zone | |
| Complete integration with surrounding cartilage | 4 |
| Demarcating border <1 mm | 3 |
| ¾th of graft integrated, ¼th with a notable border >1 mm width | 2 |
| ½ of graft integrated with surrounding cartilage, ½ with a notable border >1 mm | 1 |
| From no contact to ¼th of graft integrated with surrounding cartilage | 0 |
| Macroscopic appearance | |
| Intact smooth surface | 4 |
| Fibrillated surface | 3 |
| Small, scattered fissures or cracs | 2 |
| Several, small or few but large fissures | 1 |
| Total degeneration of grafted area | 0 |
| Overall repair assessment | |
| Grade I: normal | 12 |
| Grade II: nearly normal | 11-8 |
| Grade III: abnormal | 7-4 |
| Grade IV: severely abnormal | 3-1 |

TABLE 3

| Variable | Comment | Score |
|---|---|---|
| Tissue Morphology (TI) | Mostly hyaline cartilage | 4 |
| | Mostly fibrocartilage | 3 |
| | Mostly non-cartilage | 2 |
| | Exclusively non-cartilage | 1 |

TABLE 3-continued

| Variable | Comment | Score |
|---|---|---|
| Matrix staining (Matx) | None | 1 |
| | Slight | 2 |
| | Moderate | 3 |
| | Strong | 4 |
| Structural integrity (Stru) | Severe desintegration | 1 |
| | Cysts or disruption | 2 |
| | No organization of chondrocytes | 3 |
| | Beginning of columnar organization of chondrocytes | 4 |
| | Normal, similar to healthy mature cartilage | 5 |
| Chondrocyte clustering in implant (Clus) | 25-100% of the cells clustered | 1 |
| | <25% of the cells clustered | 2 |
| | No clusters | 3 |
| Intactness of the calcified layer, formation of tidemark (Tide) | <25% of the calcified layers intact | 1 |
| | 25-49% of the calcified layer intact | 2 |
| | 50-75% of the calcified layer intact | 3 |
| | 76-90% of the calcified layer intact | 4 |
| | Complete intactness of the calcified cartilage layer | 5 |
| Subchondral bone formation (Bform) | No formation | 1 |
| | Slight | 2 |
| | Strong | 3 |
| Histological appraisal of surface architecture (SurfH) | Severe fibrillation of disruption | 1 |
| | Moderate fibrillation or irregularity | 2 |
| | Slight fibrilation or irregularity | 3 |
| | Normal | 4 |
| Histological appraisal defect filling (FilH) | <25% | 1 |
| | 26-50% | 2 |
| | 51-75% | 3 |
| | 76-90% | 4 |
| | 91-110% | 5 |
| Lateral integration of implanted material (LatI) | Not bonded | 1 |
| | Bonded at one hand/partially both ends | 2 |
| | Bonded at both sides | 3 |
| Basal integration of implanted material (BasI) | <50% | 1 |
| | 50-70% | 2 |
| | 70-90% | 3 |
| | 91-100% | 4 |
| Inflammation (InfH) | No inflammation | 1 |
| | Slight inflammation | 3 |
| | Strong inflammation | 5 |
| Maximum total score | | 45 |

Figure 3:
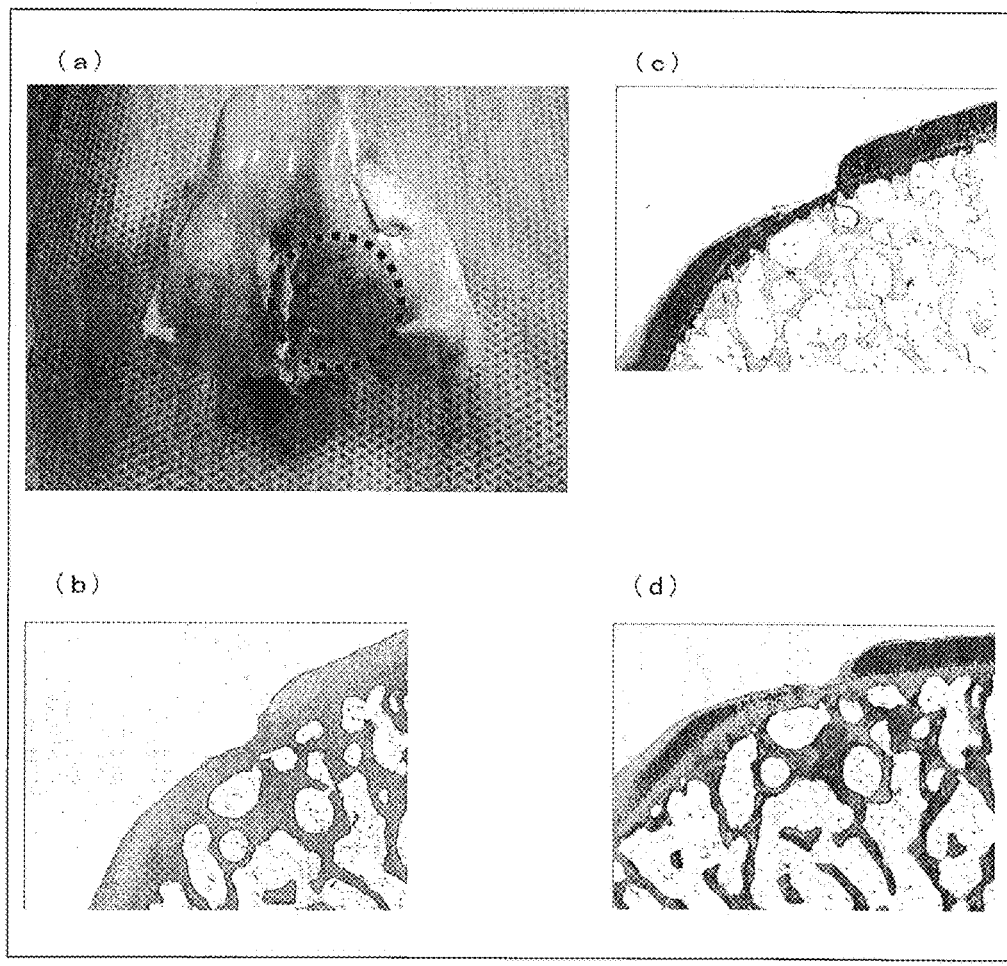
FIG. 3 is a diagram showing macroscopic and microscopic images in a case where a single administration of a cell administration solution containing $5 \times 10^5$ MSCs and 1 mL of lactated Ringer's was carried out with respect to a site of a half-thickness defect of a cartilage. (a) of FIG. 3 shows a macroscopic image. (b) of FIG. 3 shows a hematoxylin and eosin staining image. (c) of FIG. 3 shows a toluidine blue staining image. (d) of FIG. 3 shows a safranin O staining image.

FIG. 3 shows, as a comparative example, a result of an experiment using a cell administration solution which did not contain hyaluronic acid. In other words, FIG. 3 shows macroscopic and microscopic images in a case where a cell administration solution containing $5 \times 10^5$ MSCs and 1 mL of lactated Ringer's was administered to the site of the half-thickness defect of the cartilage. (a) of FIG. 3 shows a macroscopic image of the site of the half-thickness defect of the cartilage. (b) of FIG. 3 shows a hematoxylin and eosin staining image of a portion enclosed by a dotted line in (a) of FIG. 3. (c) of FIG. 3 shows a toluidine blue staining image of the portion enclosed by the dotted line in (a) of FIG. 3. (d) of FIG. 3 shows a safranin O staining image of the portion enclosed by the dotted line in (a) of FIG. 3. (a) to (d) of each of FIGS. 4 to 14 following FIG. 3 show images as in FIG. 3. In the state of FIG. 3, the ICRS score was 2, and the modified O'Driscoll histological score was 13.

Figure 4:
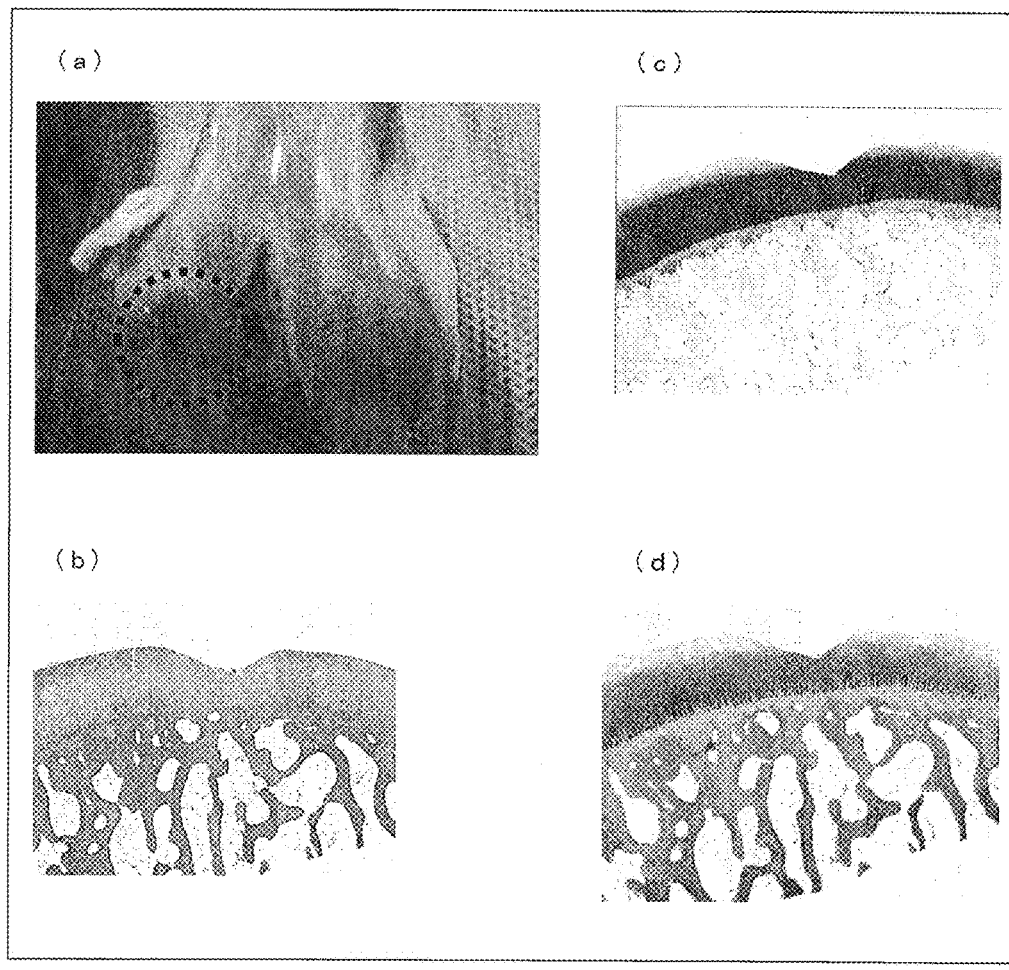
FIG. 4 is a diagram showing macroscopic and microscopic images in a case where a single administration of a cell administration solution containing $5 \times 10^5$ MSCs, 990 µL of lactated Ringer's, and 10 µL of 1% hyaluronic acid (hyaluronic acid concentration of the cell administration solution: 0.01%) was carried out with respect to the site of the half-thickness defect of the cartilage. (a) of FIG. 4 shows a macroscopic image. (b) of FIG. 4 shows a hematoxylin and eosin staining image. (c) of FIG. 4 shows a toluidine blue staining image. (d) of FIG. 4 shows a safranin O staining image.

FIG. 4 shows macroscopic and microscopic images in a case where a cell administration solution containing $5 \times 10^5$ MSCs, 990 µL of lactated Ringer's, and 10 µL of 1% hyaluronic acid (hyaluronic acid concentration of the cell administration solution: 0.01%) was administered to the site of the half-thickness defect of the cartilage. In the state of FIG. 4, the ICRS score was 3, and the modified O'Driscoll histological score was 17.

Figure 5:
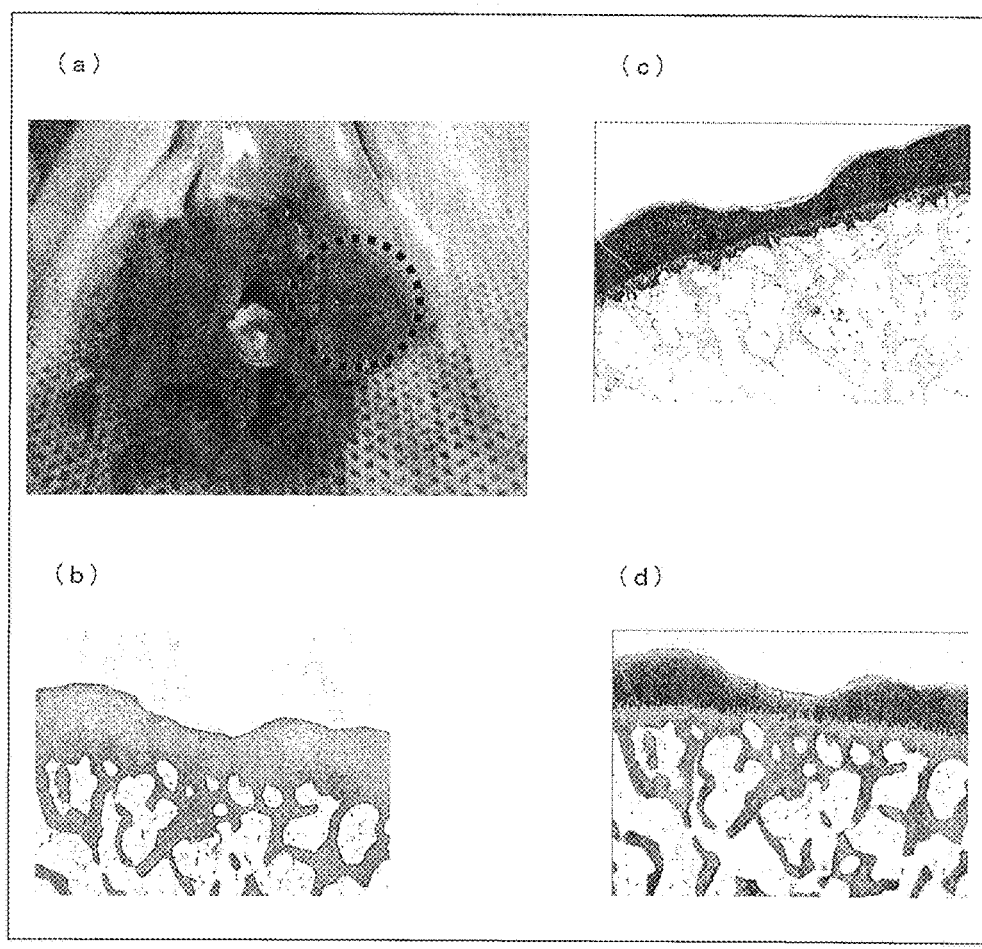
FIG. 5 is a diagram showing macroscopic and microscopic images in a case where a single administration of a cell administration solution containing $5 \times 10^5$ MSCs, 900 µL of lactated Ringer's, and 100 µL of 1% hyaluronic acid (hyaluronic acid concentration of the cell administration solution: 0.1%) was carried out with respect to the site of the half-thickness defect of the cartilage. (a) of FIG. 5 shows a macroscopic image. (b) of FIG. 5 shows a hematoxylin and eosin staining image. (c) of FIG. 5 shows a toluidine blue staining image. (d) of FIG. 5 shows a safranin O staining image.

FIG. 5 shows macroscopic and microscopic images in a case where a cell administration solution containing $5 \times 10^5$ MSCs, 900 µL of lactated Ringer's, and 100 µL of 1% hyaluronic acid (hyaluronic acid concentration of the cell administration solution: 0.1%) was administered to the site of the half-thickness defect of the cartilage. In the state of FIG. 5, the ICRS score was 2, and the modified O'Driscoll histological score was 17.

Figure 6:
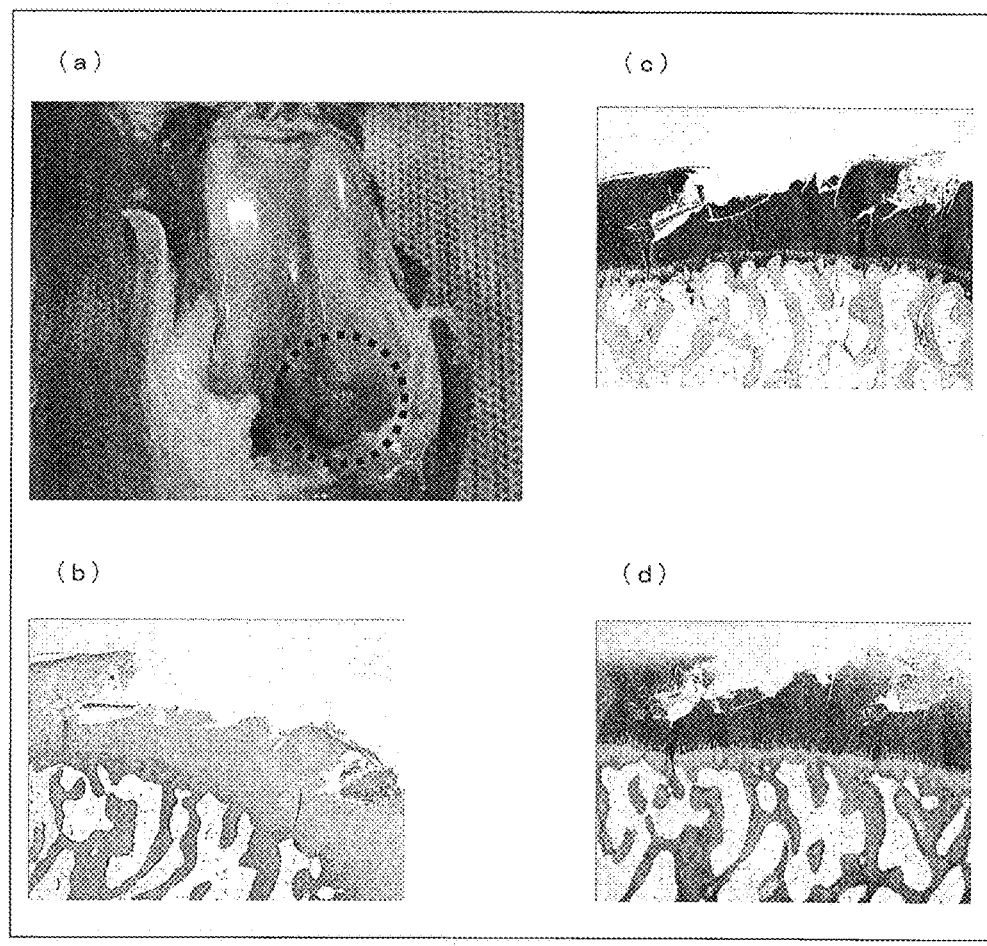
FIG. 6 is a diagram showing macroscopic and microscopic images in a case where a single administration of a cell administration solution containing $5 \times 10^5$ MSCs, 500 µL of lactated Ringer's, and 500 µL of 1% hyaluronic acid (hyaluronic acid concentration of the cell administration solution: 0.5%) was carried out with respect to the site of the half-thickness defect of the cartilage. (a) of FIG. 6 shows a macroscopic image. (b) of FIG. 6 shows a hematoxylin and eosin staining image. (c) of FIG. 6 shows a toluidine blue staining image. (d) of FIG. 6 shows a safranin O staining image.

FIG. 6 shows macroscopic and microscopic images in a case where a cell administration solution containing $5 \times 10^5$ MSCs, 500 µL of lactated Ringer's, and 500 µL of 1% hyaluronic acid (hyaluronic acid concentration of the cell administration solution: 0.5%) was administered to the site of the half-thickness defect of the cartilage. In the state of FIG. 6, the ICRS score was 2, and the modified O'Driscoll histological score was 16.

Figure 7:
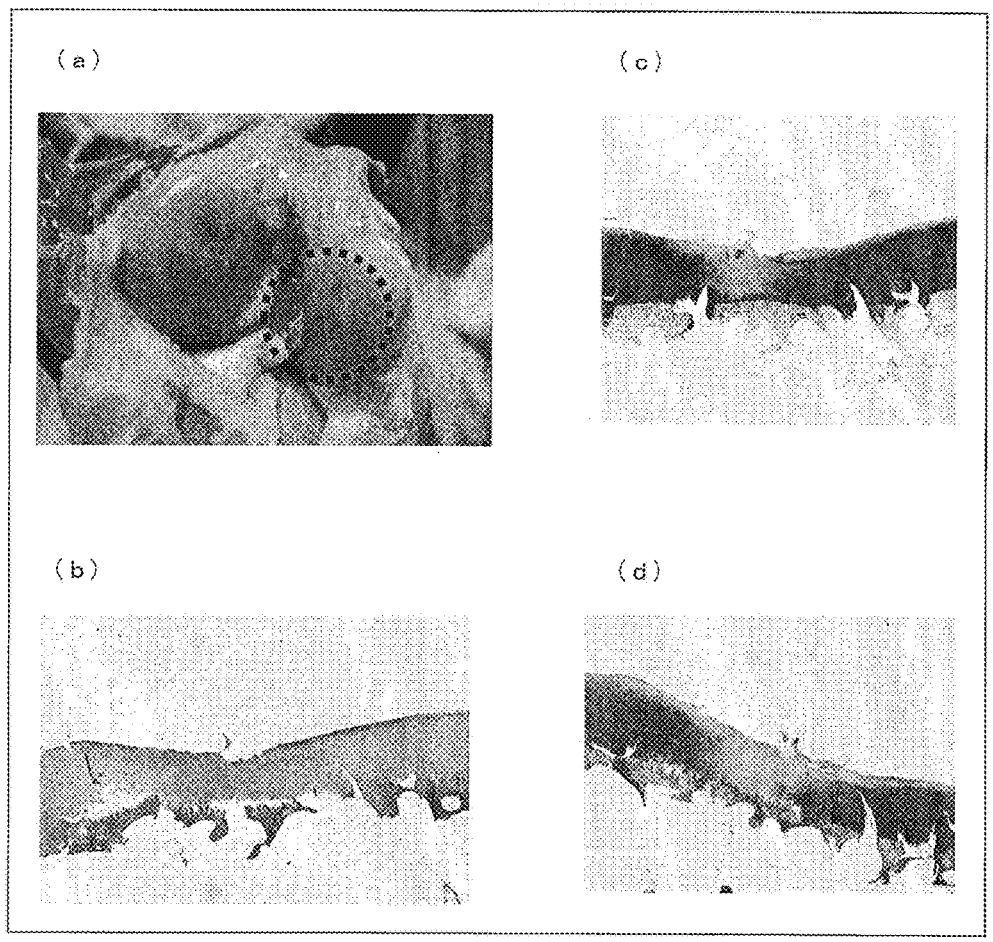
FIG. 7 is a diagram showing macroscopic and microscopic images in a case where a single administration of a cell administration solution containing $5 \times 10^6$ MSCs and 1 mL of lactated Ringer's was carried out with respect to the site of the half-thickness defect of the cartilage. (a) of FIG. 7 shows a macroscopic image. (b) of FIG. 7 shows a hematoxylin and eosin staining image. (c) of FIG. 7 shows a toluidine blue staining image. (d) of FIG. 7 shows a safranin O staining image.

FIG. 7 shows, as a comparative example, a result of an experiment using a cell administration solution which did not contain hyaluronic acid. That is, FIG. 7 shows macroscopic and microscopic images in a case where a cell administration solution containing $5 \times 10^6$ MSCs and 1 mL of lactated Ringer's was administered to the site of the half-thickness defect of the cartilage. In the state of FIG. 7, the ICRS score was 2, and the modified O'Driscoll histological score was 14.

Figure 8:
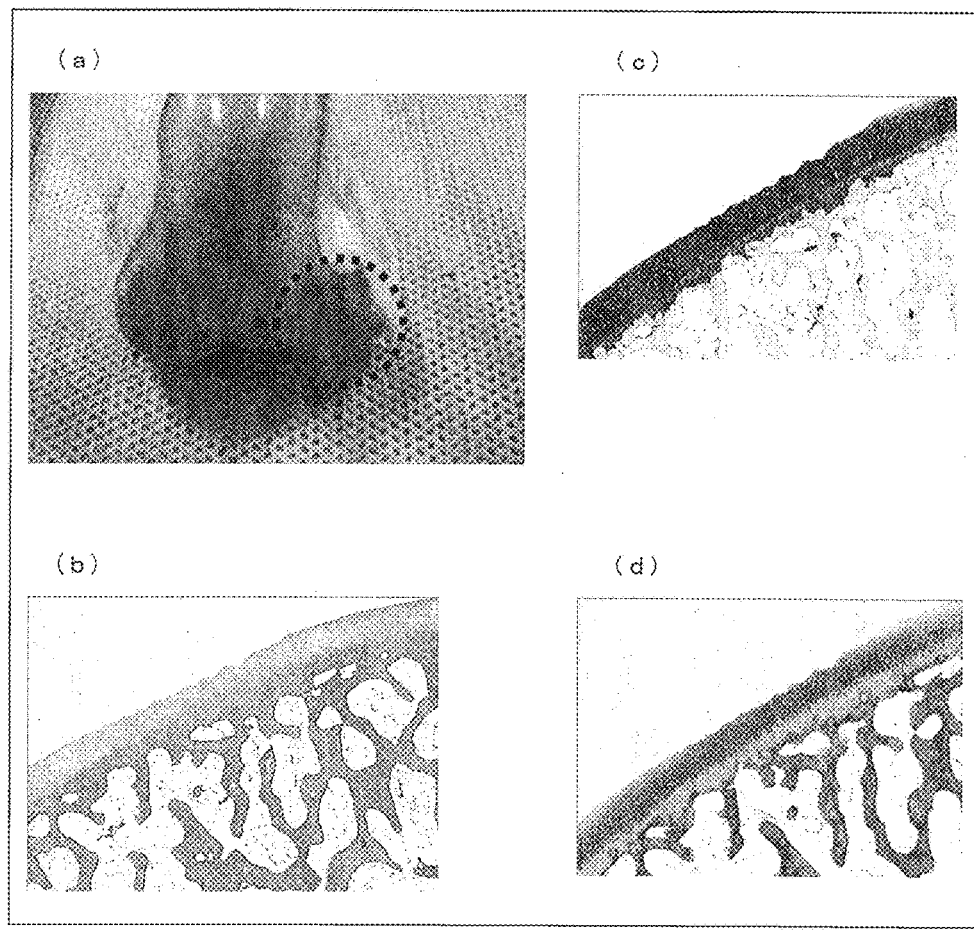
FIG. 8 is a diagram showing macroscopic and microscopic images in a case where a single administration of a cell administration solution containing $5 \times 10^6$ MSCs, 990 µL of lactated Ringer's, and 10 µL of 1% hyaluronic acid (hyaluronic acid concentration of the cell administration solution: 0.01%) was carried out with respect to the site of the half-thickness defect of the cartilage. (a) of FIG. 8 shows a macroscopic image. (b) of FIG. 8 shows a hematoxylin and eosin staining image. (c) of FIG. 8 shows a toluidine blue staining image. (d) of FIG. 8 shows a safranin O staining image.

FIG. 8 shows macroscopic and microscopic images in a case where a cell administration solution containing $5 \times 10^6$ MSCs, 990 µL of lactated Ringer's, and 10 µL of 1% hyaluronic acid (hyaluronic acid concentration of the cell administration solution: 0.01%) was administered to the site of the half-thickness defect of the cartilage. In the state of FIG. 8, the ICRS score was 11, and the modified O'Driscoll histological score was 39.

Figure 9:
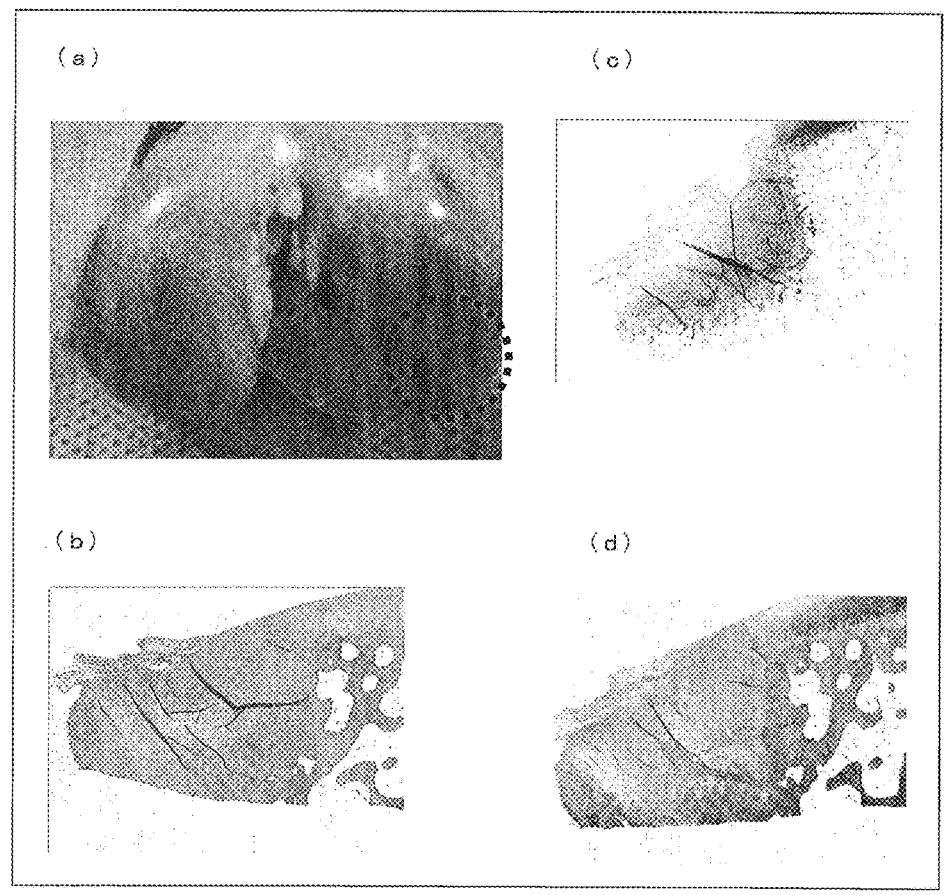
FIG. 9 is a diagram showing macroscopic and microscopic images in a case where a single administration of a cell administration solution containing $5 \times 10^6$ MSCs, 900 µL of lactated Ringer's, and 100 µL of 1% hyaluronic acid (hyaluronic acid concentration of the cell administration solution: 0.1%) was carried out with respect to the site of the half-thickness defect of the cartilage. (a) of FIG. 9 shows a macroscopic image. (b) of FIG. 9 shows a hematoxylin and eosin staining image. (c) of FIG. 9 shows a toluidine blue staining image. (d) of FIG. 9 shows a safranin O staining image.

FIG. 9 shows macroscopic and microscopic images in a case where a cell administration solution containing $5 \times 10^6$ MSCs, 900 µL of lactated Ringer's, and 100 µL of 1% hyaluronic acid (hyaluronic acid concentration of the cell administration solution: 0.1%) was administered to the site of the half-thickness defect of the cartilage. In the state of FIG. 9, the ICRS score was 4, and the modified O'Driscoll histological score was 19.

Figure 10:
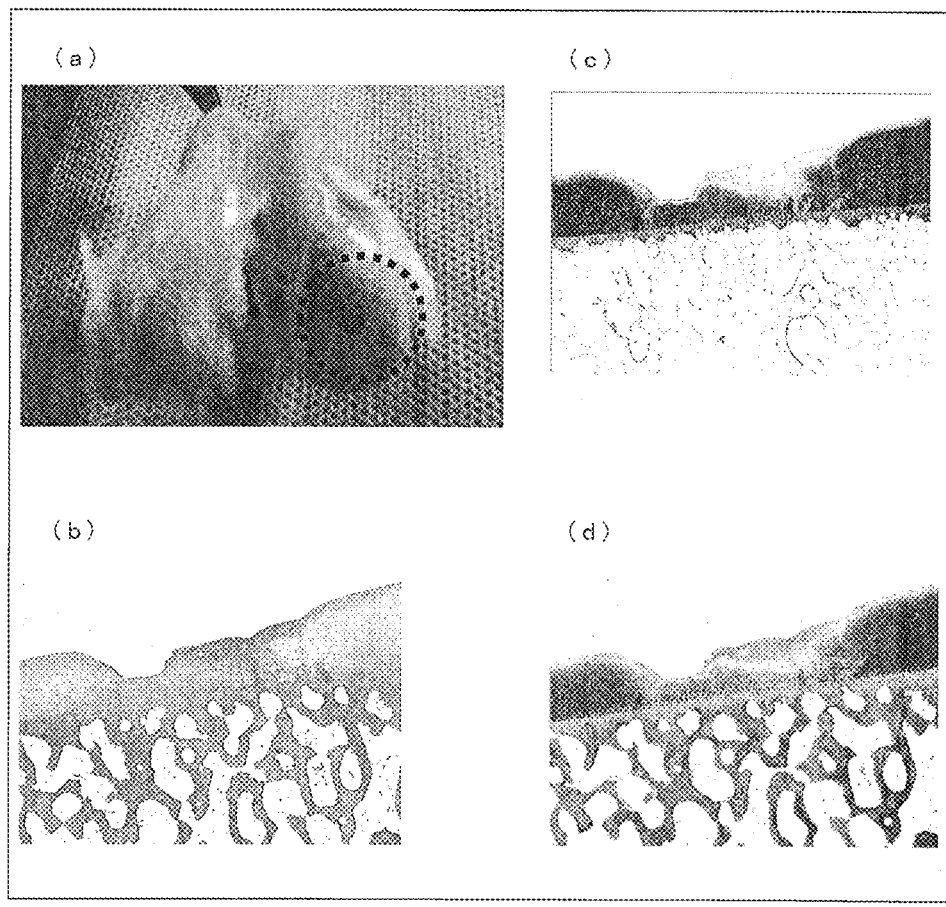
FIG. 10 is a diagram showing macroscopic and microscopic images in a case where a single administration of a cell administration solution containing $5 \times 10^6$ MSCs, 500 µL of lactated Ringer's, and 500 µL of 1% hyaluronic acid (hyaluronic acid concentration of the cell administration solution: 0.5%) was carried out with respect to the site of the half-thickness defect of the cartilage. (a) of FIG. 10 shows a macroscopic image. (b) of FIG. 10 shows a hematoxylin and eosin staining image. (c) of FIG. 10 shows a toluidine blue staining image. (d) of FIG. 10 shows a safranin O staining image.

FIG. 10 shows macroscopic and microscopic images in a case where a cell administration solution containing $5 \times 10^6$ MSCs, 500 µL of lactated Ringer's, and 500 µL of 1% hyaluronic acid (hyaluronic acid concentration of the cell administration solution: 0.5%) was administered to the site of the half-thickness defect of the cartilage. In the state of FIG. 10, the ICRS score was 2, and the modified O'Driscoll histological score was 15.

Figure 11:
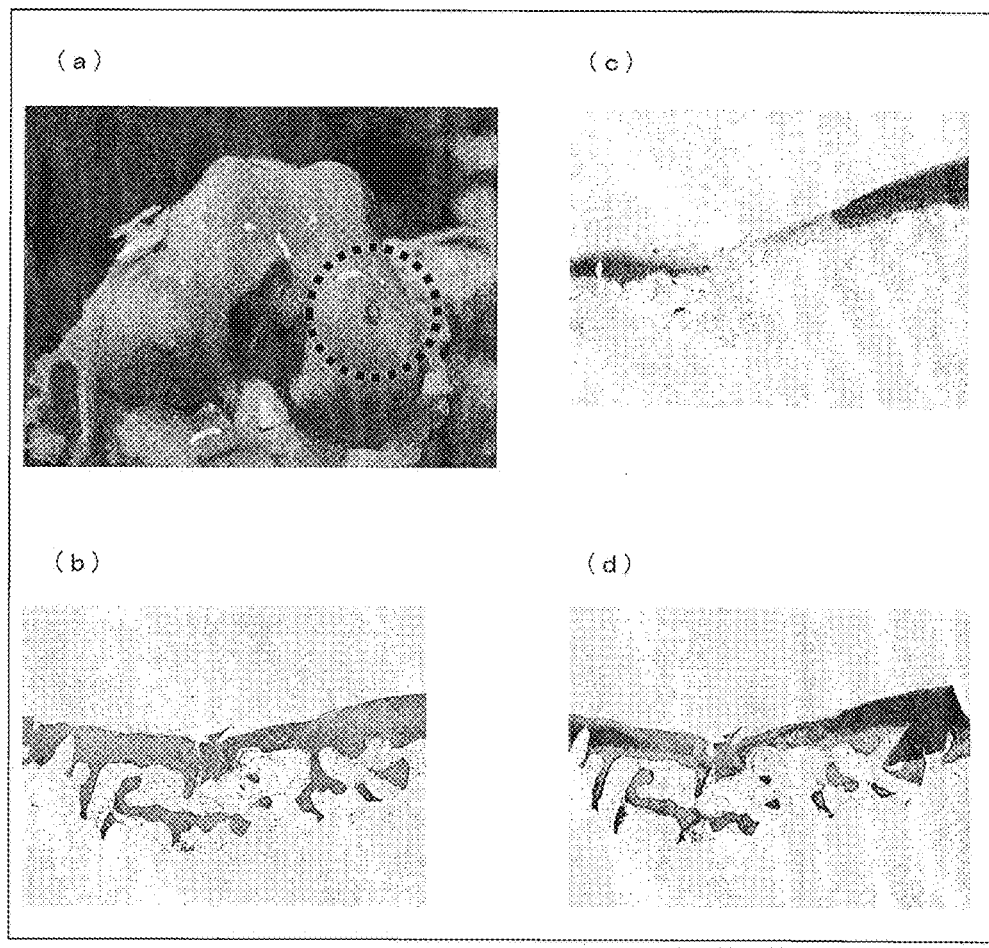
FIG. 11 is a diagram showing macroscopic and microscopic images in a case where a single administration of a cell administration solution containing $5 \times 10^7$ MSCs and 1 mL of lactated Ringer's was carried out with respect to the site of the half-thickness defect of the cartilage. (a) of FIG. 11 shows a macroscopic image. (b) of FIG. 11 shows a hematoxylin and eosin staining image. (c) of FIG. 11 shows a toluidine blue staining image. (d) of FIG. 11 shows a safranin O staining image.

FIG. 11 shows, as a comparative example, a result of an experiment using a cell administration solution which did not contain hyaluronic acid. That is, FIG. 11 shows macroscopic and microscopic images in a case where a cell administration solution containing $5 \times 10^7$ MSCs and 1 mL of lactated Ringer's was administered to the site of the half-thickness defect of the cartilage. In the state of FIG. 11, the ICRS score was 2, and the modified O'Driscoll histological score was 17.

Figure 12:
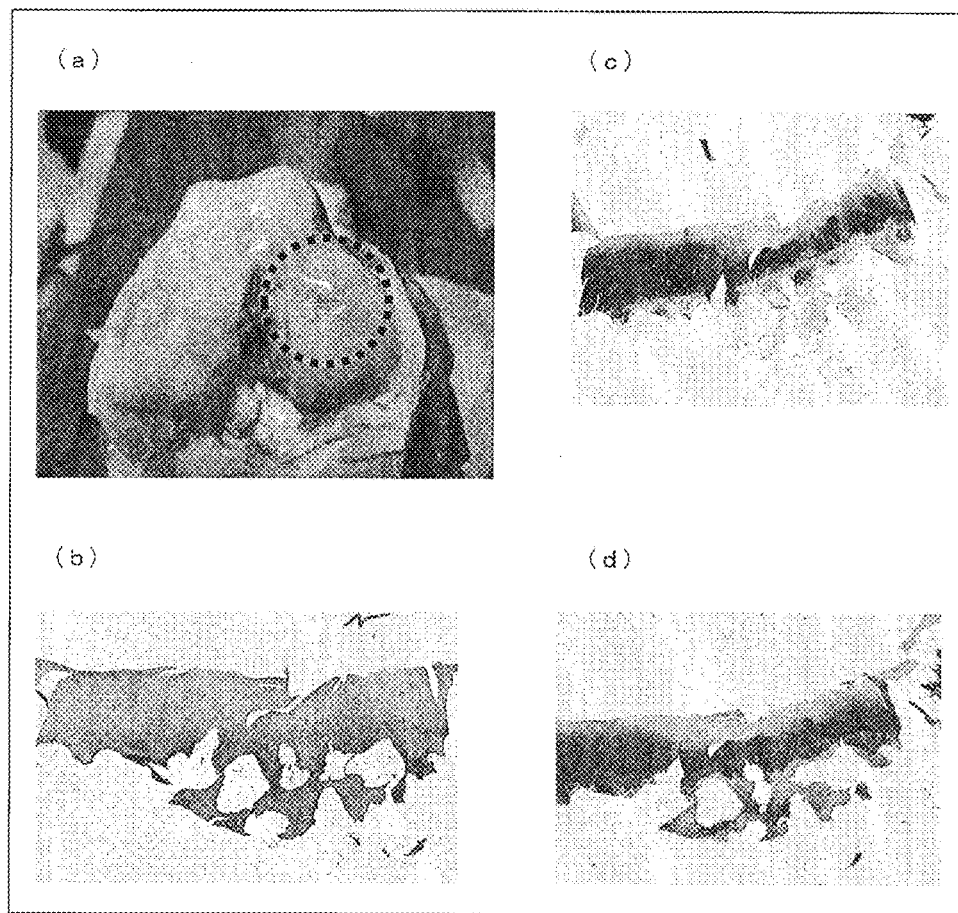
FIG. 12 is a diagram showing macroscopic and microscopic images in a case where a single administration of a cell administration solution containing $5 \times 10^7$ MSCs, 500 µL of lactated Ringer's, and 500 µL of 1% hyaluronic acid (hyaluronic acid concentration of the cell administration solution: 0.5%) was carried out with respect to the site of the half-thickness defect of the cartilage. (a) of FIG. 12 shows a macroscopic image. (b) of FIG. 12 shows a hematoxylin and eosin staining image. (c) of FIG. 12 shows a toluidine blue staining image. (d) of FIG. 12 shows a safranin O staining image.

FIG. 12 shows macroscopic and microscopic images in a case where a cell administration solution containing $5 \times 10^7$ MSCs, 500 µL of lactated Ringer's, and 500 µL of 1% hyaluronic acid (hyaluronic acid concentration of the cell administration solution: 0.5%) was administered to the site of the half-thickness defect of the cartilage. In the state of FIG. 12, the ICRS score was 2, and the modified O'Driscoll histological score was 16.

Figure 13:
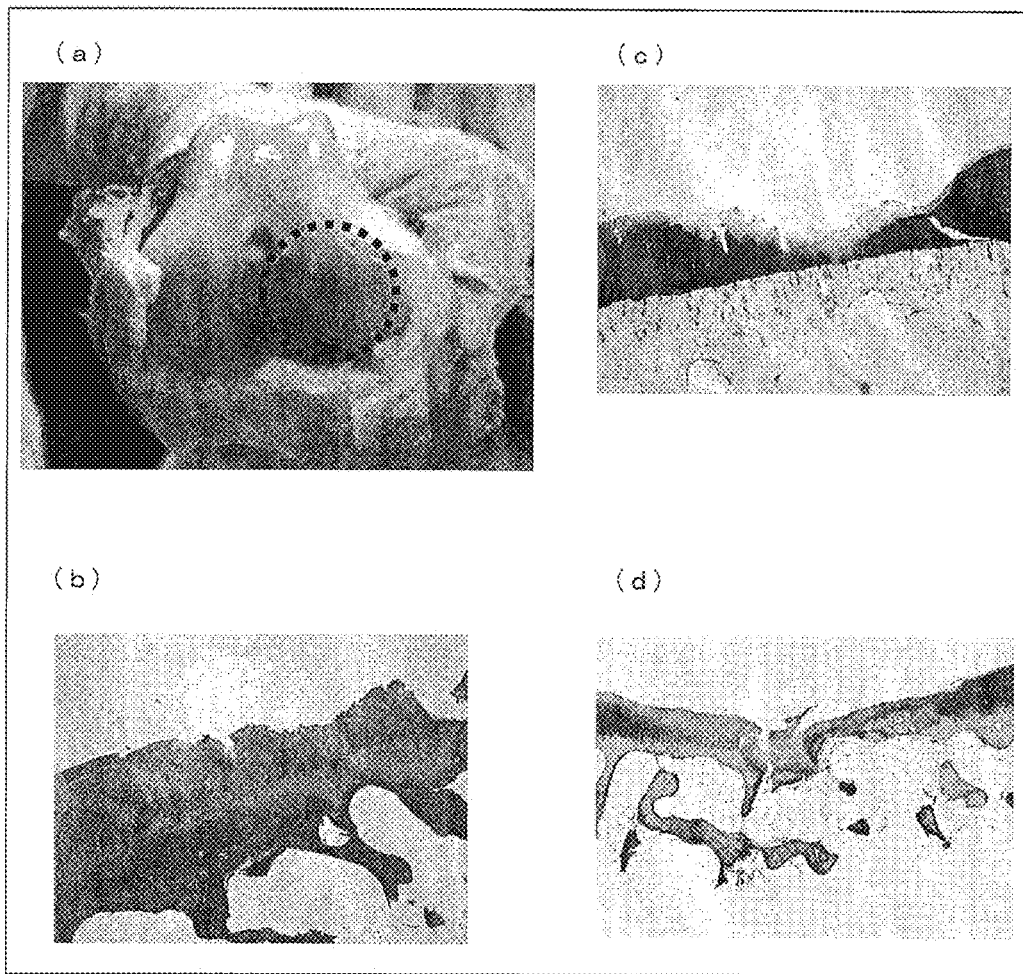
FIG. 13 is a diagram showing macroscopic and microscopic images in a case where a single administration of an administration solution containing only 1 mL of lactated Ringer's was carried out with respect to the site of the half-thickness defect of the cartilage. (a) of FIG. 13 shows a macroscopic image. (b) of FIG. 13 shows a hematoxylin and eosin staining image. (c) of FIG. 13 shows a toluidine blue staining image. (d) of FIG. 13 shows a safranin O staining image.

FIG. 13 shows, as a comparative example, a result of an experiment using an administration solution which contained neither an MSC nor hyaluronic acid. That is, FIG. 13 shows macroscopic and microscopic images in a case where an administration solution containing only 1 mL of lactated Ringer's was administered to the site of the half-thickness defect of the cartilage. In the state of FIG. 13, the ICRS score was 1, and the modified O'Driscoll histological score was 11.

Figure 14:
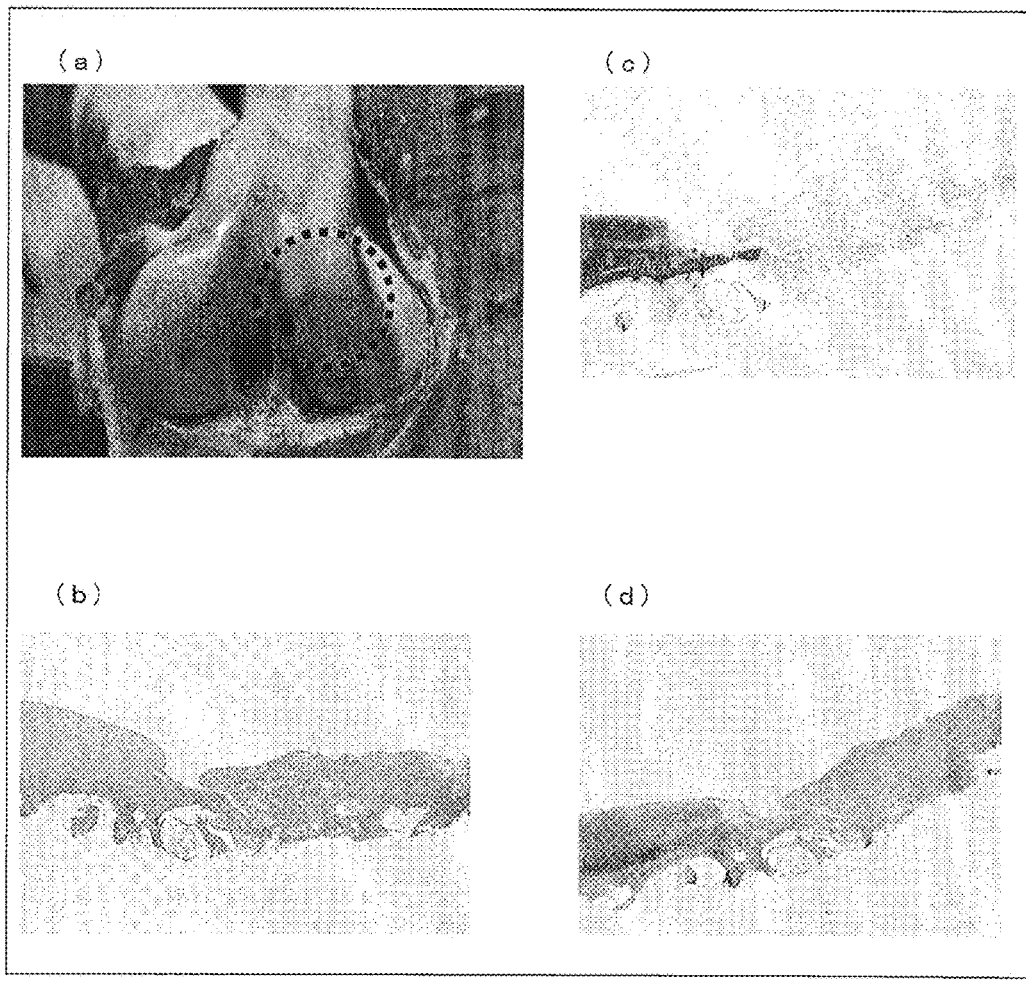
FIG. 14 is a diagram showing macroscopic and microscopic images in a case where a single administration of an administration solution containing 500 µL of lactated Ringer's and 500 µL of 1% hyaluronic acid (hyaluronic acid concentration of the administration solution: 0.5%) was carried out with respect to the site of the half-thickness defect of the cartilage. (a) of FIG. 14 shows a macroscopic image. (b) of FIG. 14 shows a hematoxylin and eosin staining image. (c) of FIG. 14 shows a toluidine blue staining image. (d) of FIG. 14 shows a safranin O staining image.

FIG. 14 shows, as a comparative example, a result of an experiment using an administration solution which did not contain any MSC. That is, FIG. 14 shows macroscopic and microscopic images in a case where an administration solution containing 500 μL of lactated Ringer's and 500 μL of 1% hyaluronic acid (hyaluronic acid concentration of the administration solution: 0.5%) was administered to the site of the half-thickness defect of the cartilage. In the state of FIG. 14, the ICRS score was 1, and the modified O'Driscoll histological score was 11.

Figure 15:
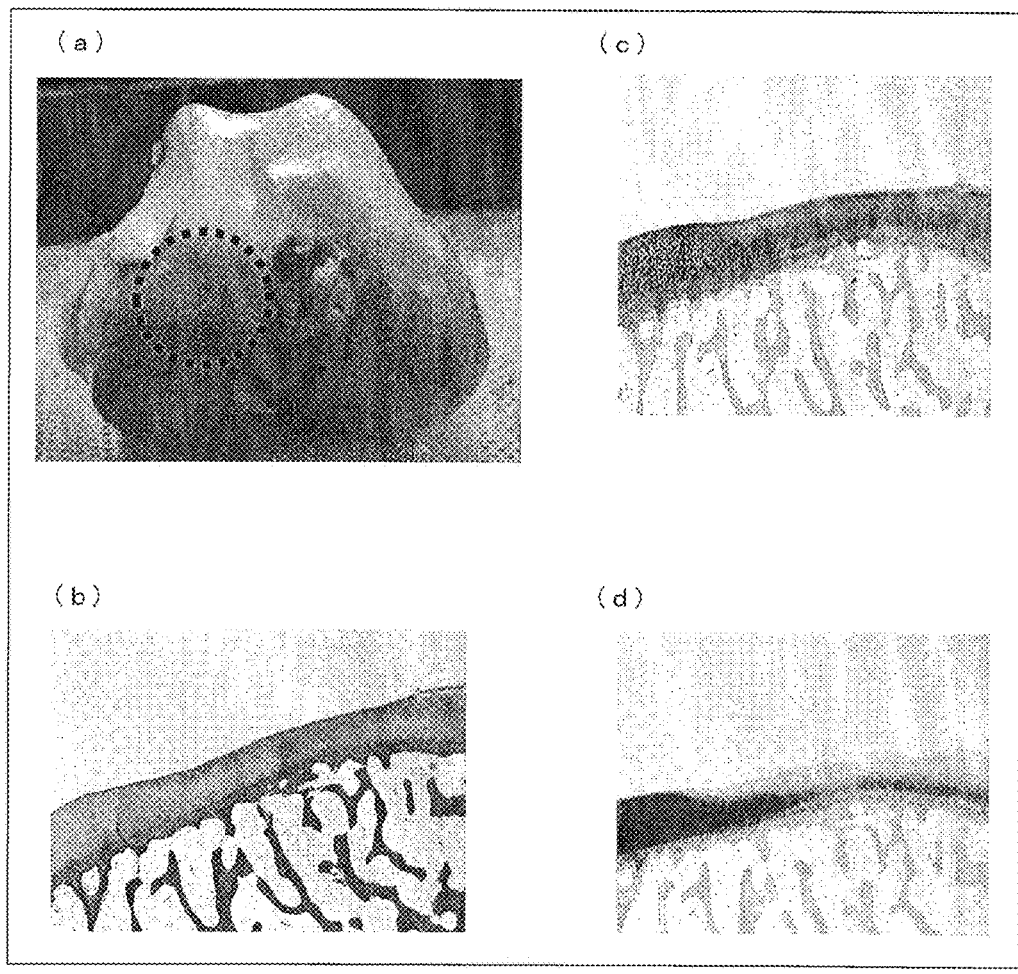
FIG. 15 is a diagram showing macroscopic and microscopic images in a case where a single administration of a cell administration solution containing $5 \times 10^7$ MSCs, 990 µL of lactated Ringer's, and 10 µL of 1% hyaluronic acid (hyaluronic acid concentration of the cell administration solution: 0.01%) was carried out with respect to the site of the half-thickness defect of the cartilage. (a) of FIG. 15 shows a macroscopic image. (b) of FIG. 15 shows a hematoxylin and eosin staining image. (c) of FIG. 15 shows a type II collagen staining image. (d) of FIG. 15 shows a safranin O staining image.

FIG. 15 shows macroscopic and microscopic images in a case where a cell administration solution containing $5 \times 10^7$ MSCs, 990 μL of lactated Ringer's, and 10 μL of 1% hyaluronic acid (hyaluronic acid concentration of the cell administration solution: 0.01%) was administered to the site of the half-thickness defect of the cartilage. (a) of FIG. 15 shows a macroscopic image of the site of the half-thickness defect of the cartilage. (b) of FIG. 15 shows a hematoxylin and eosin staining image of a portion enclosed by a dotted line in (a) of FIG. 15. (c) of FIG. 15 shows a type II collagen staining image of the portion enclosed by the dotted line in (a) of FIG. 15. (d) of FIG. 15 shows a safranin O staining image of the portion enclosed by the dotted line in (a) of FIG. 15. In the state of FIG. 15, the ICRS score was 11, and the modified O'Driscoll histological score was 37.

Figure 16:
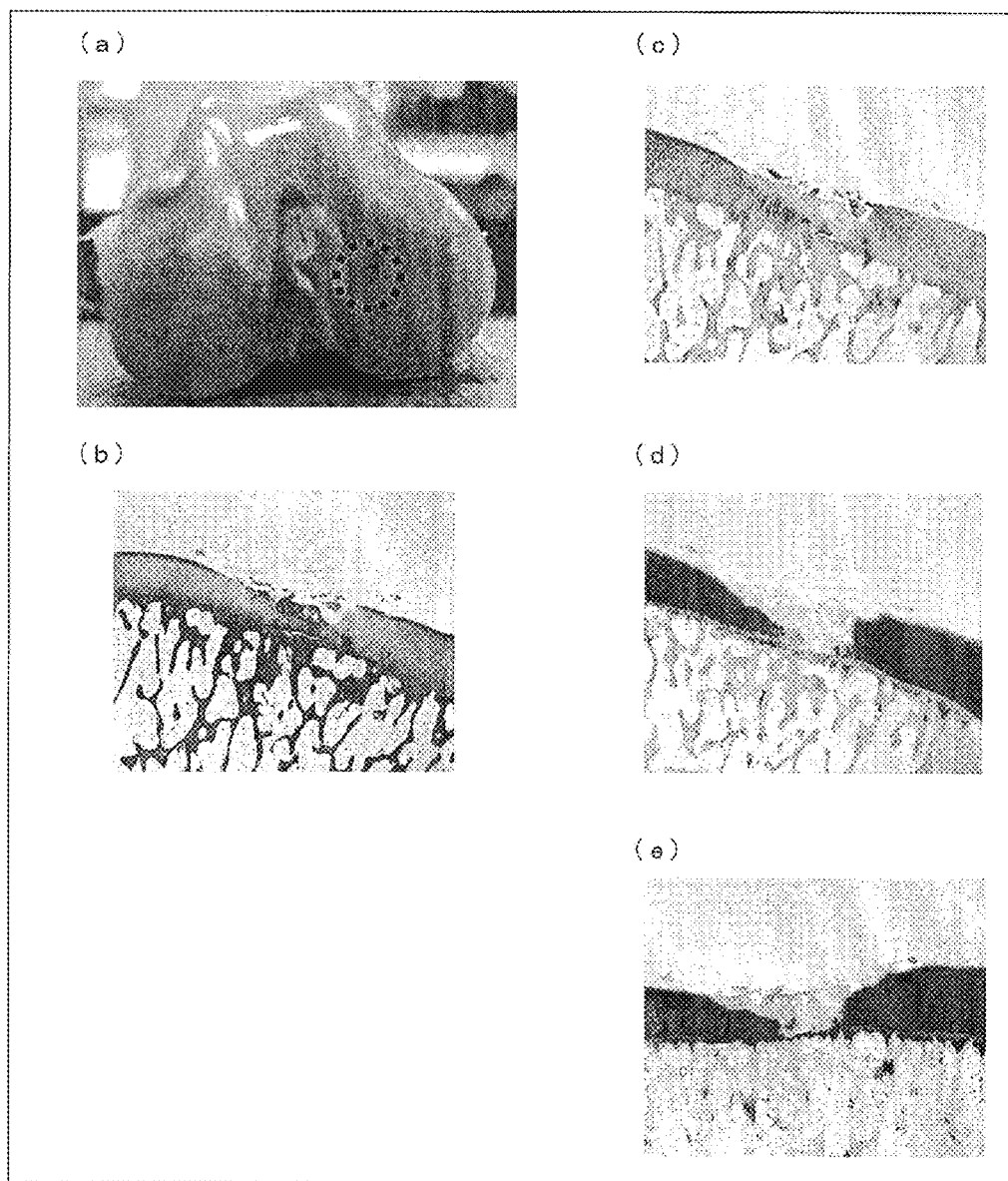
FIG. 16 is a diagram showing macroscopic and microscopic images in a case where a single administration of a cell administration solution containing 5×10$^7$ MSCs, 900 µL of lactated Ringer's, and 100 µL of 1% hyaluronic acid (hyaluronic acid concentration of the cell administration solution: 0.1%) was carried out with respect to the site of the half-thickness defect of the cartilage. (a) of FIG. 16 shows a macroscopic image. (b) of FIG. 16 shows a hematoxylin and eosin staining image. (c) of FIG. 16 shows a type II collagen staining image. (d) of FIG. 16 shows a safranin O staining image. (e) of FIG. 16 shows a toluidine blue staining image.

FIG. 16 shows macroscopic and microscopic images in a case where a cell administration solution containing $5 \times 10^7$ MSCs, 900 μL of lactated Ringer's, and 100 μL of 1% hyaluronic acid (hyaluronic acid concentration of the cell administration solution: 0.1%) was administered to the site of the half-thickness defect of the cartilage. The descriptions of (a) to (d) of FIG. 15 apply to (a) to (d) of FIG. 16. (e) of FIG. 16 shows a toluidine blue staining image of the portion enclosed by the dotted line in (a) of FIG. 16. In the state of FIG. 16, the ICRS score was 3, and the modified O'Driscoll histological score was 18.

It was found on the basis of the ICRS score and the modified O'Driscoll histological score for each combination of the number of cells and the hyaluronic acid concentration, that the cartilage tissues can be most favorably regenerated with the cell administration solution containing $5 \times 10^6$ MSCs, 990 μL of lactated Ringer's, and 10 μL of 1% hyaluronic acid (hyaluronic acid concentration of the cell administration solution: 0.01%). On the other hand, it was found that when the hyaluronic acid concentration becomes high, cartilage regeneration is inhibited. Further, influence on a walking ability and a health condition such as the occurrence of infection was very little on the dog after operation.

Figure 17:
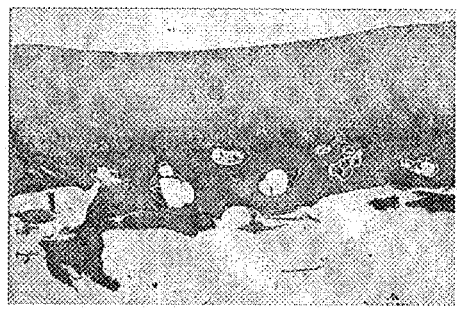
FIG. 17 is a diagram showing microscopic images of a healthy cartilage in a joint to which a single administration of a cell administration solution was carried out. (a) of FIG. 17 shows a hematoxylin and eosin staining image. (b) of FIG. 17 shows a toluidine blue staining image. (c) of FIG. 17 shows a safranin O staining image.
Figure 17:
Figure 17:
Figure 18:
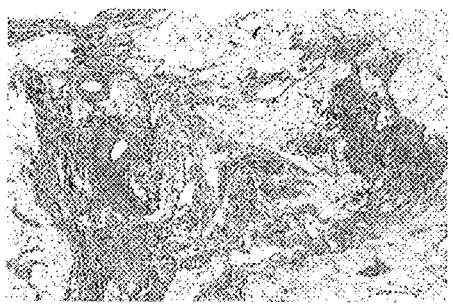
FIG. 18 is a diagram showing microscopic images of a healthy synovial membrane in a joint to which a single administration of a cell administration solution was carried out. (a) of FIG. 18 shows a hematoxylin and eosin staining image. (b) of FIG. 18 shows a toluidine blue staining image. (c) of FIG. 18 shows a safranin O staining image.
Figure 18:
Figure 18:

Further, in the cartilage defect model of the dog to which a cell administration solution was administered, a healthy intra-articular cartilage and a healthy synovial membrane were stained as described above, and the occurrence of dysplasia was assessed. FIG. 17 shows microscopic images of a healthy cartilage in a joint to which the cell administration solution was administered. (a) of FIG. 17 shows a hematoxylin and eosin staining image. (b) of FIG. 17 shows a toluidine blue staining image. (c) of FIG. 17 shows a safranin O staining image. FIG. 18 shows microscopic images of a healthy synovial membrane in a joint to which the cell administration solution was administered. (a) of FIG. 18 shows a hematoxylin and eosin staining image. (b) of FIG. 18 shows a toluidine blue staining image. (c) of FIG. 18 shows a safranin O staining image. As shown in FIGS. 17 and 18, no clear dysplasia was found in the healthy joint.

Figure 19:
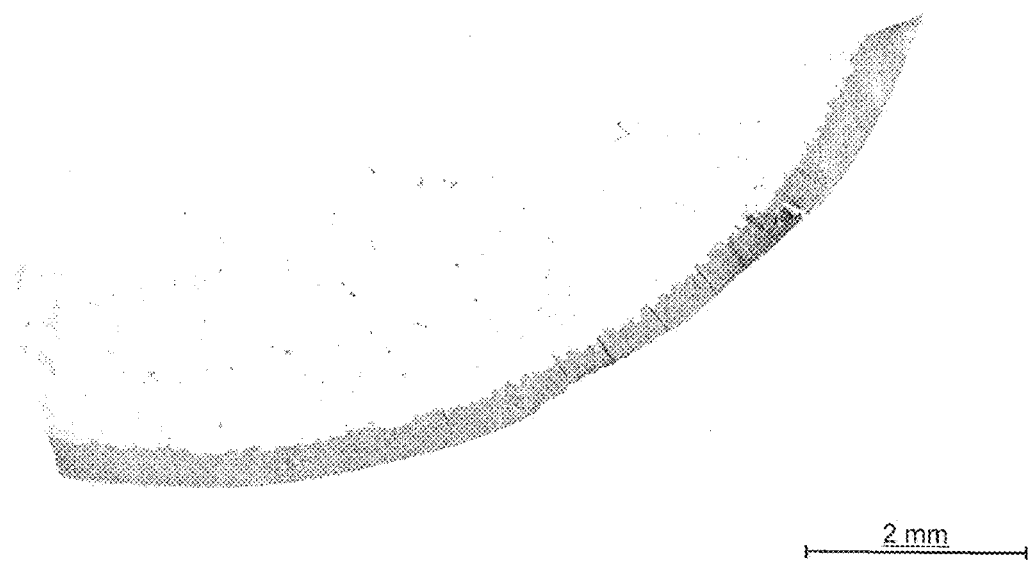
FIG. 19 is a diagram showing a microscopic view (low magnification) in a case where by using a cell administration solution which had provided the best result and contained 5×10$^6$ MSCs, 990 µL of lactated Ringer's, and 10 µL of 1% hyaluronic acid (hyaluronic acid concentration of the cell administration solution: 0.01%), type II collagen immunostaining was carried out on an individual having the site of the half-thickness defect of the cartilage to which site a single administration of the cell administration solution was carried out.
Figure 20:
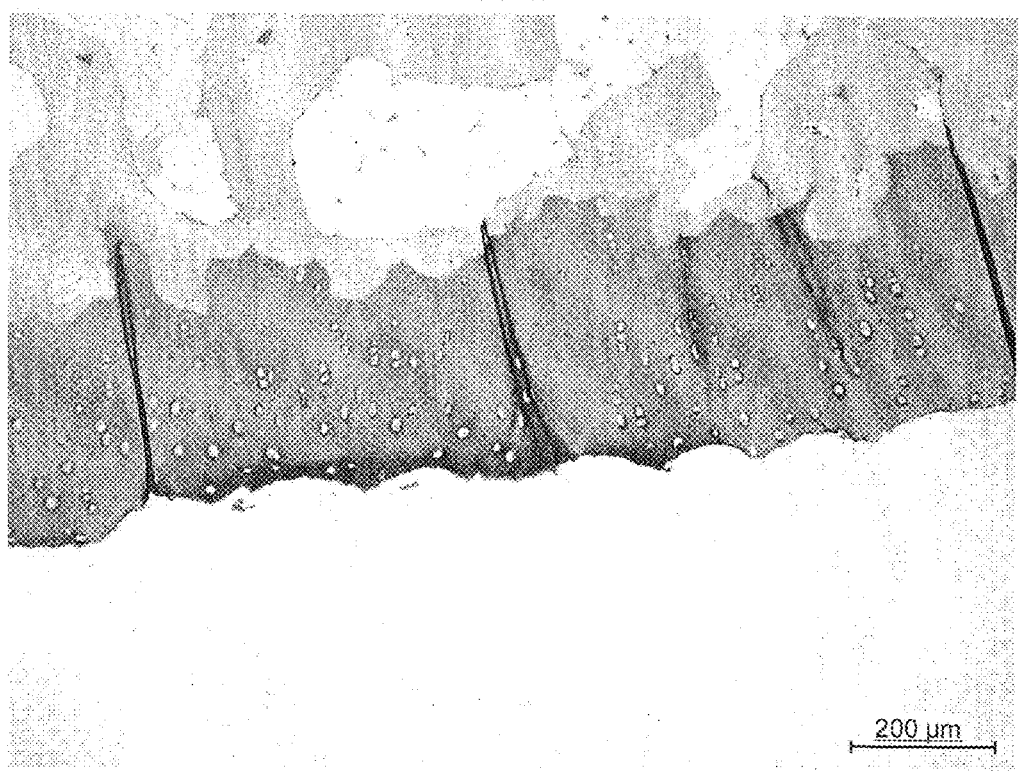
FIG. 20 is a diagram showing a microscopic view (high magnification) in a case where by using a cell administration solution which had provided the best result and contained 5×10$^6$ MSCs, 990 µL of lactated Ringer's, and 10 µL of 1% hyaluronic acid (hyaluronic acid concentration of the cell administration solution: 0.01%), type II collagen immunostaining was carried out on an individual having the site of the half-thickness defect of the cartilage to which site a single administration of the cell administration solution was carried out.
Figure 21:
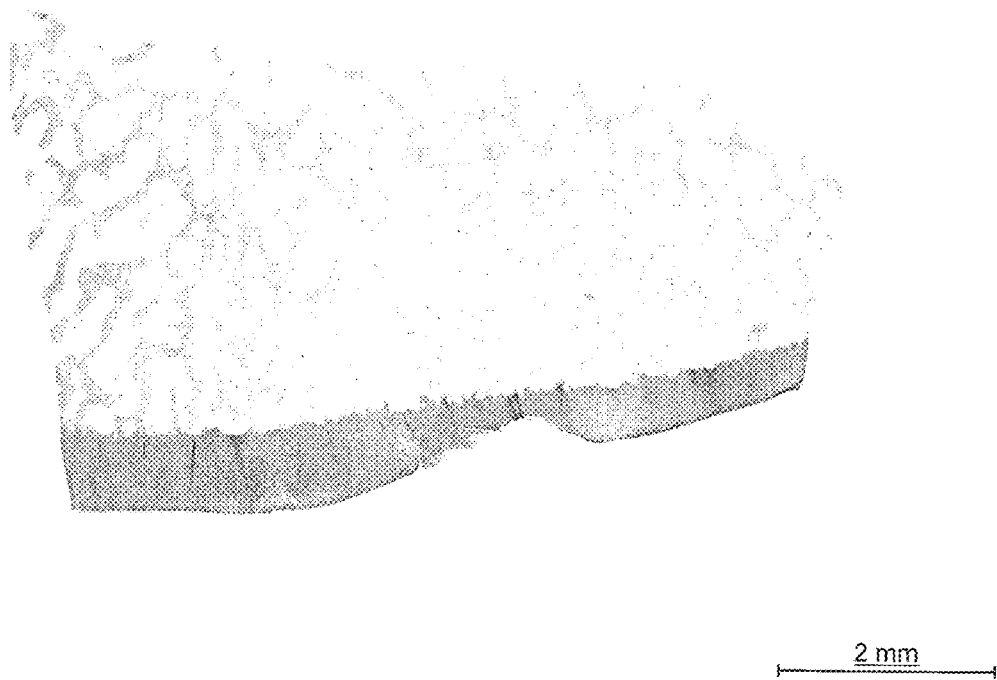
FIG. 21 is a diagram showing a microscopic view (low magnification) in a case where by using an administration solution which had provided no cartilage generation and contained only 1 mL of lactated Ringer's, type II collagen immunostaining was carried out on an individual having the site of the half-thickness defect of the cartilage to which site a single administration of the cell administration solution was carried out.
Figure 22:
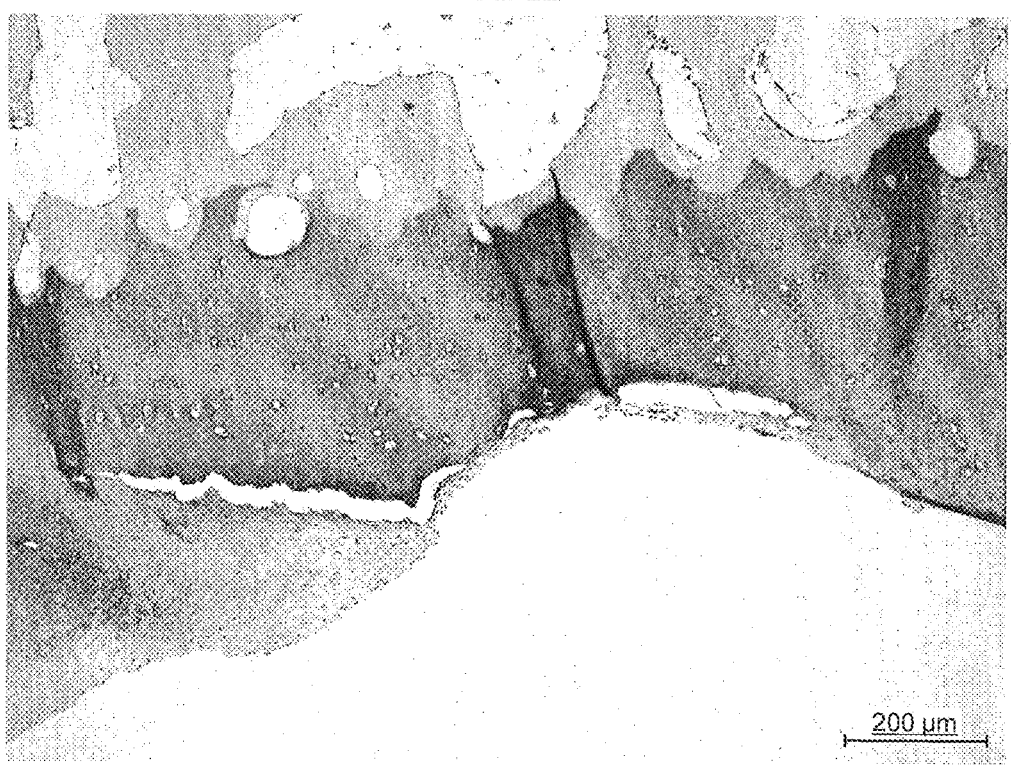
FIG. 22 is a diagram showing a microscopic view (high magnification) in a case where by using an administration solution which had provided no cartilage generation and contained only 1 mL of lactated Ringer's, type II collagen immunostaining was carried out on an individual having the site of the half-thickness defect of the cartilage to which site a single administration of the cell administration solution was carried out.

As a wrap-up, by using a cell administration solution which had provided the best result and contained $5 \times 10^6$ MSCs, 990 μL of lactated Ringer's, and 10 μL of 1% hyaluronic acid (hyaluronic acid concentration of the cell administration solution: 0.01%), type II collagen immunostaining was carried out on an individual having the site of the half-thickness defect of the cartilage to which site this cell administration solution was administered. As a result, a microscopic image of the type II collagen immunostaining was obtained. FIG. 19 shows a magnified view (low magnification) of the microscopic image and FIG. 20 shows a magnified view (high magnification) of the microscopic image. Further, by using an administration solution which had provided no cartilage generation and contained only 1 mL of lactated Ringer's, type II collagen immunostaining was carried out on an individual having the site of the half-thickness defect of the cartilage to which site this administration solution was administered. As a result, a microscopic image of the type II collagen immunostaining was obtained. FIG. 21 shows a magnified view (low magnification) of the microscopic image and FIG. 22 shows a magnified view (high magnification) of the microscopic image.

FIGS. 19 and 20 show the most favorable result. These FIGS. 19 and 20 each show a type II collagen immunostaining image of the site of the half-thickness defect of the cartilage to which site the cell administration solution containing $5 \times 10^6$ MSCs, 990 μL of lactated Ringer's, and 10 μL of 1% hyaluronic acid (hyaluronic acid concentration of the cell administration solution: 0.01%) was administered. FIGS. 21 and 22 each show a type II collagen immunostaining image of the site of the half-thickness defect of the cartilage to which site the administration solution containing only 1 mL of lactated Ringer's was administered.

As shown in FIGS. 19 to 22, the cartilage was favorably regenerated by administrating the cell administration solution containing $5 \times 10^6$ MSCs, 990 μL of lactated Ringer's, and 10 μL of 1% hyaluronic acid (hyaluronic acid concentration of the cell administration solution: 0.01%) to the site of the half-thickness defect of the cartilage.

(4. Intra-Articular Administrations (Multiple Administrations))

<Method>

As in the method in the above "3. Intra-articular Administration (Single Administration)", (a) a cell administration solution containing $5 \times 10^6$ MSCs, 990 μL of lactated Ringer's, and 10 μL of 1% hyaluronic acid (hyaluronic acid concentration of the cell administration solution: 0.01%) and (b) a cell administration solution containing $5 \times 10^6$ MSCs, 900 μL of lactated Ringer's, and 100 μL of 1% hyaluronic acid (hyaluronic acid concentration of the cell administration solution: 0.1%) were prepared. Thus prepared cell administration solutions were transported to an animal experimentation facility (refrigerated storage for 5 to 21 hours), and each were put into a syringe. Then, each of the prepared cell administration solutions was administered three times into the joint (the site of the half-thickness defect of the cartilage of the knee joint) of the cartilage defect model of the dog prepared in the above "1. Cell Culturing".

A dosage of the cell administration solution was 1 mL each time and an interval between administrations was 7 days.

<Results>

After 12 weeks from the third administration, the site of the half-thickness defect of the cartilage was observed and slices of the site were prepared. Thus prepared slices were subjected to various stainings such as hematoxylin and eosin staining, toluidine blue staining, safranin O staining, and type II collagen staining. Then, a state of repair at the site of the defect was evaluated by microscope observation as in the above "3. Intra-articular Administration (Single Administration)".

Figure 23:
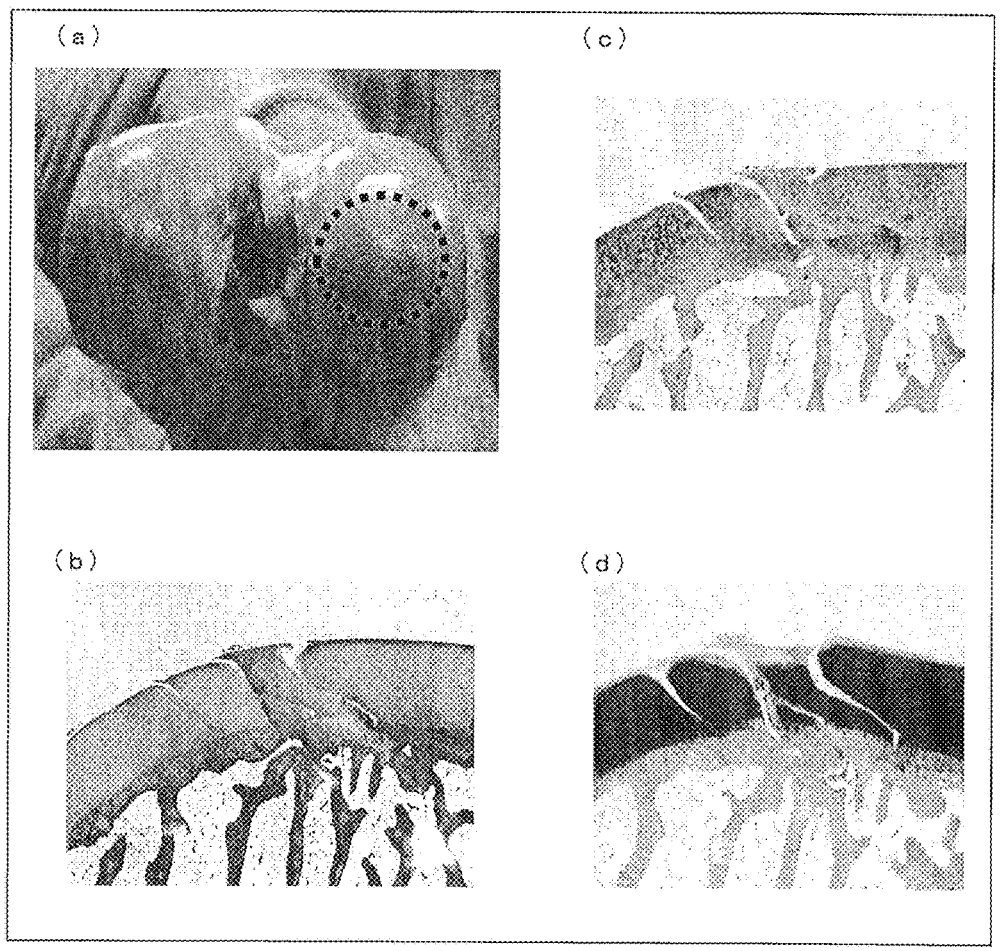
FIG. 23 is a diagram showing macroscopic and microscopic images in a case where a cell administration solution containing 5×10$^6$ MSCs, 990 µL of lactated Ringer's, and 10 µL of 1% hyaluronic acid (hyaluronic acid concentration of the cell administration solution: 0.01%) was administered three times with respect to the site of the half-thickness defect of the cartilage. (a) of FIG. 23 shows a macroscopic image. (b) of FIG. 23 shows a hematoxylin and eosin staining image. (c) of FIG. 23 shows a type II collagen staining image. (d) of FIG. 23 shows a safranin O staining image.

FIG. 23 shows macroscopic and microscopic images in a case where a cell administration solution containing $5 \times 10^6$ MSCs, 990 µL of lactated Ringer's, and 10 µL of 1% hyaluronic acid (hyaluronic acid concentration of the cell administration solution: 0.01%) was administered three times to the site of the half-thickness defect of the cartilage. (a) of FIG. 23 shows a macroscopic image of the site of the half-thickness defect of the cartilage. (b) of FIG. 23 shows a hematoxylin and eosin staining image of a portion enclosed by a dotted line in (a) of FIG. 23. (c) of FIG. 23 shows a type II collagen staining image of the portion enclosed by the dotted line in (a) of FIG. 23. (d) of FIG. 23 shows a safranin O staining image of the portion enclosed by the dotted line in (a) of FIG. 23. In the state of FIG. 23, the ICRS score was 11, and the modified O'Driscoll histological score was 37.

Figure 24:
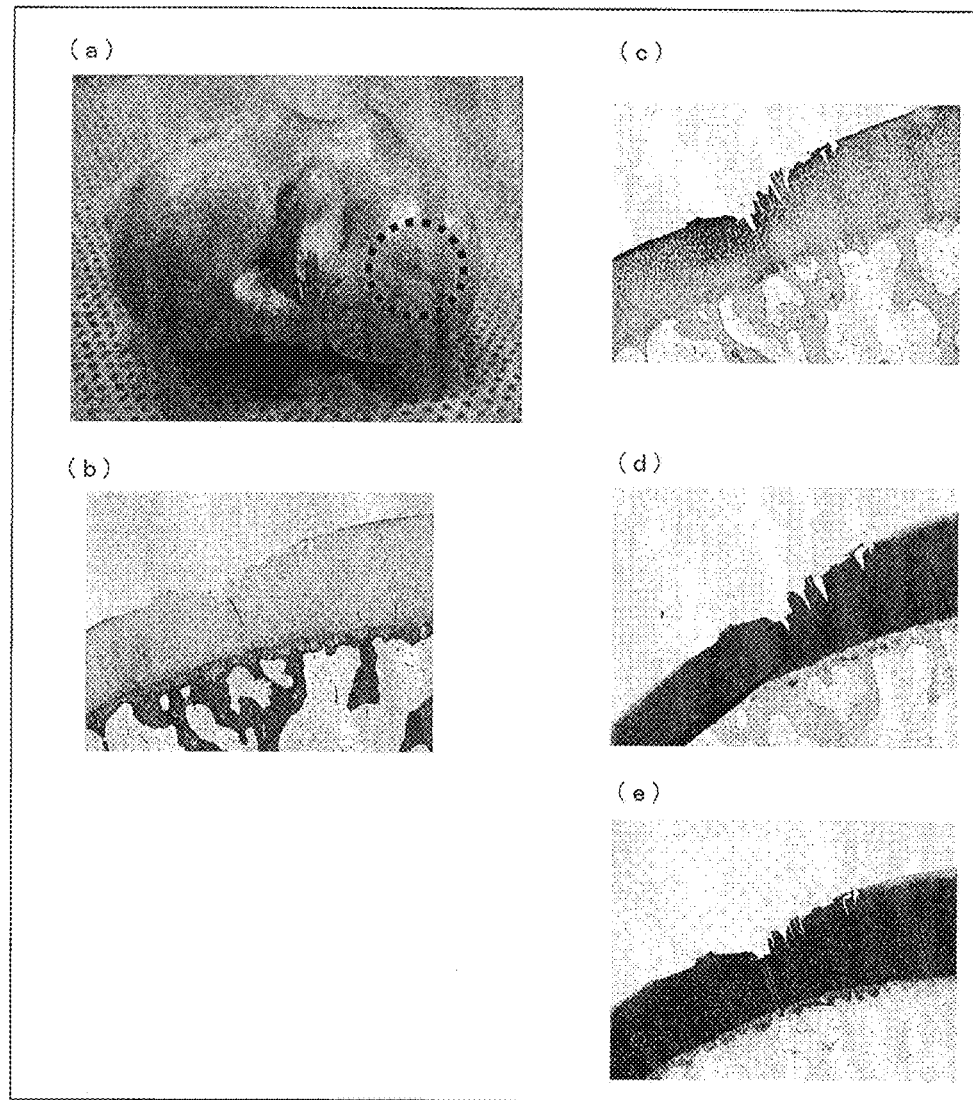
FIG. 24 is a diagram showing macroscopic and microscopic images in a case where a cell administration solution containing 5×10$^6$ MSCs, 900 µL of lactated Ringer's, and 100 µL of 1% hyaluronic acid (hyaluronic acid concentration of the cell administration solution: 0.1%) was administered three times with respect to the site of the half-thickness defect of the cartilage. (a) of FIG. 24 shows a macroscopic image. (b) of FIG. 24 shows a hematoxylin and eosin staining image. (c) of FIG. 24 shows a type II collagen staining image. (d) of FIG. 24 shows a safranin O staining image. (e) of FIG. 24 shows a toluidine blue staining image.

FIG. 24 shows macroscopic and microscopic images in a case where a cell administration solution containing $5 \times 10^6$ MSCs, 900 µL of lactated Ringer's, and 100 µL of 1% hyaluronic acid (hyaluronic acid concentration of the cell administration solution: 0.1%) was administered three times to the site of the half-thickness defect of the cartilage. The descriptions of (a) to (d) of FIG. 23 apply to (a) to (d) of FIG. 24. (e) of FIG. 24 shows a toluidine blue staining image of the portion enclosed by the dotted line in (a) of FIG. 24. In the state of FIG. 24, the ICRS score was 3, and the modified O'Driscoll histological score was 21.

II. State of MSCs in Joint Cavity (1. Undifferentiated State)

Figure 26:
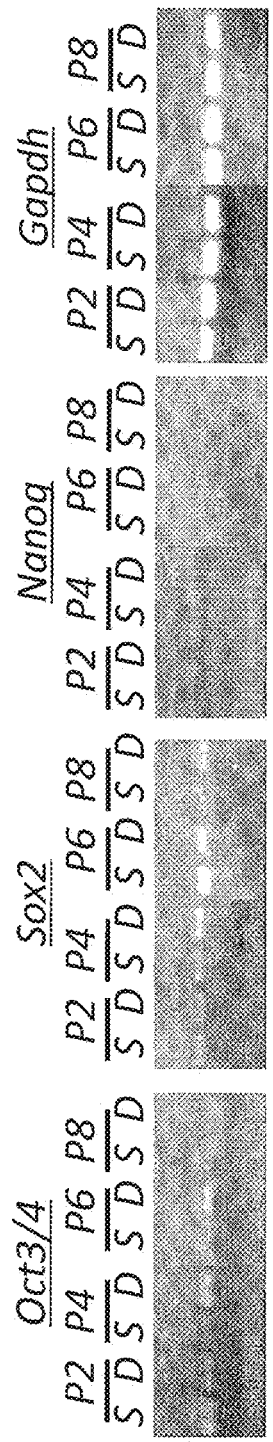
FIG. 26 is a diagram illustrating a result of measurement of expression of undifferentiation marker genes in MSCs obtained from inside a joint cavity to which a cell administration solution was administered. The letter S indicates a result of culturing in a serum-free medium, the letter D indicates a result of culturing in a serum-containing medium, and the letter P indicates the passage number.

It was checked whether or not MSCs in an undifferentiated state were present in the joint cavity to which a single administration of the cell administration solution was carried out in the above "I. Experiments on Cartilage Regeneration". First, MSCs were obtained from inside the joint cavity of an individual to which joint cavity the cell administration solution containing MSCs was administered. Then, the MSCs were cultured in each of a serum-free medium and a serum-containing medium. Thereafter, expression of undifferentiation marker genes (nanog, sox2, oct3/4) and an endogenous control gene (Gapdh) in thus cultured cells were measured. FIG. 26 shows a result of this measurement. FIG. 26 is a diagram illustrating a result of measurement of expression of undifferentiation marker genes in the MSCs obtained from inside the joint cavity to which the cell administration solution was administered. The letter S indicates a result of culturing in the serum-free medium, the letter D indicates a result of culturing in the serum-containing medium, and the letter P indicates the passage number.

As shown in FIG. 26, expression of each of the undifferentiation marker genes was found in cells cultured in both the serum-free medium and the serum-containing mediums. As a result, it was confirmed that MSCs in an undifferentiated state were present in the joint cavity to which the cell administration solution was administered.

(2. State of Cytokine Release)

A state of cytokine release was checked in the joint cavity to which a single administration of the cell administration solution was carried out in the above "I. Experiments on Cartilage Regeneration". In the joint cavity to which the cell administration solution was administered, CTACK, Eotaxin, bFGF, G-CSF, GRO-α, HGF, IFN-α2, IFN-γ, IL-1rα, IL-2, IL-2Rα, IL-3, IL-4, IL-6, IL-7, IL-8, IL-9, IL-12(p40), IL-12(p70), IL-16, IL-18, IP-10, LIF, MCP-1 (MCAF), M-CSF, MIF, MIG, β-NGF, PDGF-BB, RANTES, SCF, SCGF-β, SDF-1α, TGF-β 1, TGF-β 2, TGF-β 3, TRAIL, and VEGF were detected. Thereby, it was confirmed many cytokines were released in the joint cavity to which the cell administration solution was administered.

III. Performance Test 1 of Cytoprotective Agent (1. Cell Culturing)

Performance of the cytoprotective agent (hyaluronic acid) in storage of cells was checked. The cytoprotective agent was the one used in the above "I. Experiments on Cartilage Regeneration". As preservative solutions, the following solutions were prepared: (a) a solution containing 990 µL of lactated Ringer's and 10 µL of 1% hyaluronic acid (hyaluronic acid concentration of the solution: 0.01%); (b) a solution containing 900 µL of lactated Ringer's and 100 µL of 1% hyaluronic acid (hyaluronic acid concentration of the solution: 0.1%); and a solution containing 500 µL of lactated Ringer's and 500 µL of 1% hyaluronic acid (hyaluronic acid concentration of the solution: 0.5%). Further, 1 mL of lactated Ringer's solution and 1 mL of the serum-free medium (STK2 medium) were prepared as controls. Then, MSCs derived from human synovial membrane tissues were dispensed into each solution so that the number of MSCs in each solution would be $5 \times 10^5$ or $5 \times 10^6$, and further, the solutions were stored in a carbon dioxide gas incubator in which the temperature was kept at 37° C. (air: 95% and carbon dioxide: 5%) or in a refrigerated showcase in which the temperature was kept at 4° C. At 37° C., a viability was measured until 168 hours had elapsed after the start of storage. Meanwhile, at 4° C., a viability was measured until 5 weeks had elapsed after the start of storage.

(2. Result)

Figure 27:
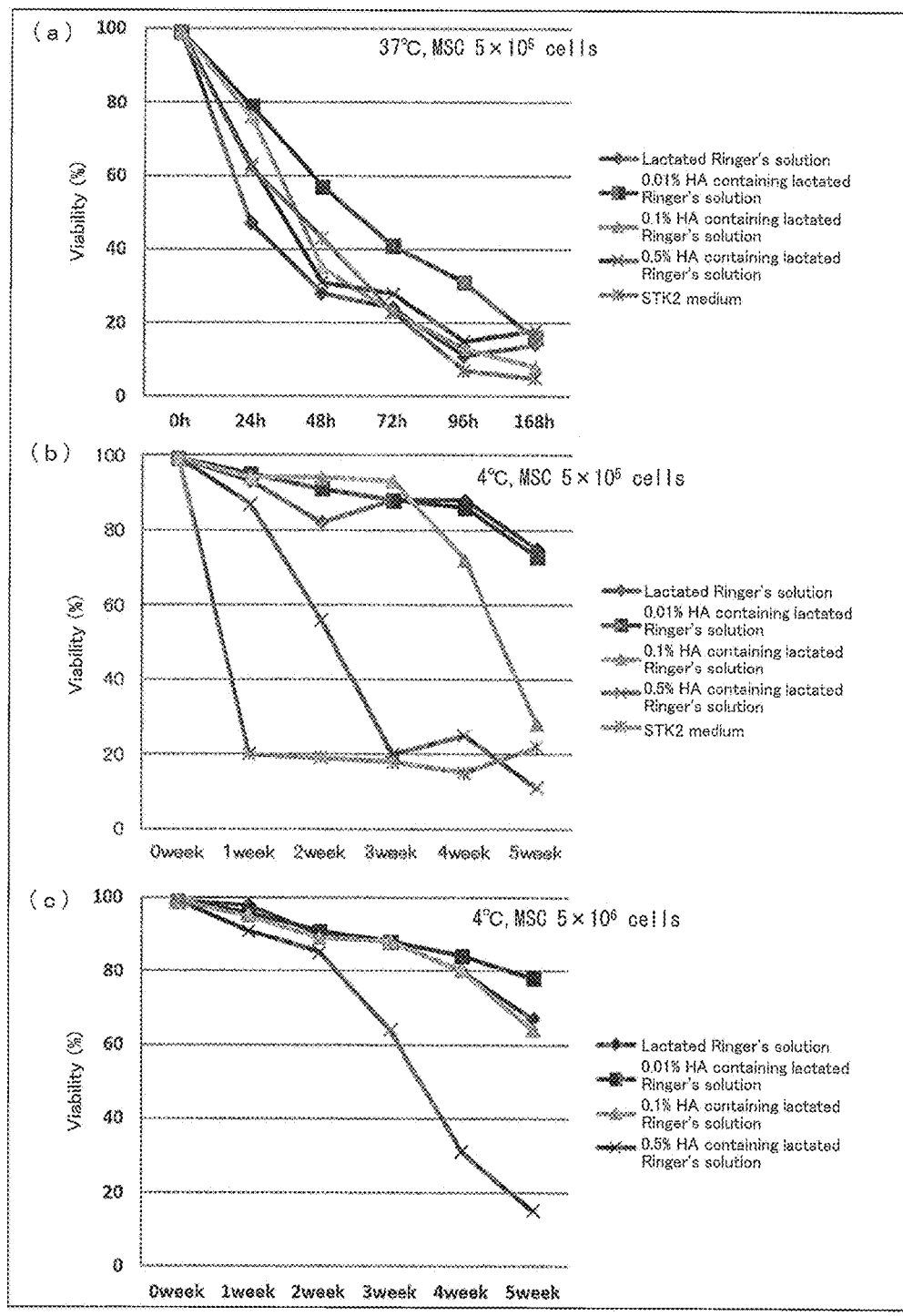
FIG. 27 is a chart showing cell viabilities over time in cases where MSCs were stored in 5 types of preservative solution: 1 mL of lactated Ringer's; a solution containing 990 µL of lactated Ringer's and 10 µL of 1% hyaluronic acid (hyaluronic acid concentration of the solution: 0.01%); a solution containing 900 µL of lactated Ringer's and 100 µL of 1% hyaluronic acid (hyaluronic acid concentration of the solution: 0.1%); a solution containing 500 µL of lactated Ringer's and 500 µL of 1% hyaluronic acid (hyaluronic acid concentration of the solution: 0.5%); and a serum-free medium (STK2 medium). (a) of FIG. 27 shows a result of a case where 5×10$^5$ MSCs were stored in an incubator at 37° C. (b) of FIG. 27 is a result of a case where 5×10$^5$ MSCs were stored under a condition refrigerated at 4° C. (c) of FIG. 27 shows a case 5×10$^6$ MSCs were stored under a condition refrigerated at 4° C.

FIG. 27 shows a result. In FIG. 27, "HA" represents "hyaluronic acid". As shown in (a) of FIG. 27, it was made clear that under a storage condition of 37° C., a solution whose hyaluronic acid concentration was 0.01% kept a higher viability as compared to the other solutions. Further, as shown in (b) and (c) of FIG. 26, it was confirmed that under a storage condition of 4° C., a solution whose hyaluronic acid concentration was 0.01%, a solution whose hyaluronic acid concentration was 0.1%, and lactated Ringer's solution were capable of keeping a viability of 60% for one month or longer.

IV. Performance Test 2 of Cytoprotective Agent (1. Cell Culturing)

The above "III. Performance Test 1 of Cytoprotective Agent" showed that even in a case where the cells are stored under a temperature condition of 37° C., the viability after 24 hours is 60% or higher in a case where the cytoprotective agent is used. Accordingly, additional experiments were carried out by using the following three solutions each provided with $5 \times 10^5$ MSCs derived from human synovial membrane tissues: (a) a solution containing 990 μL of lactated Ringer's and 10 μL of 1% hyaluronic acid (hyaluronic acid concentration of the solution: 0.01%); (b) a solution containing 900 μL of lactated Ringer's and 100 μL of 1% hyaluronic acid (hyaluronic acid concentration of the solution: 0.1%); and (c) 1 mL of lactated Ringer's solution.

(2. Result)

Figure 28:
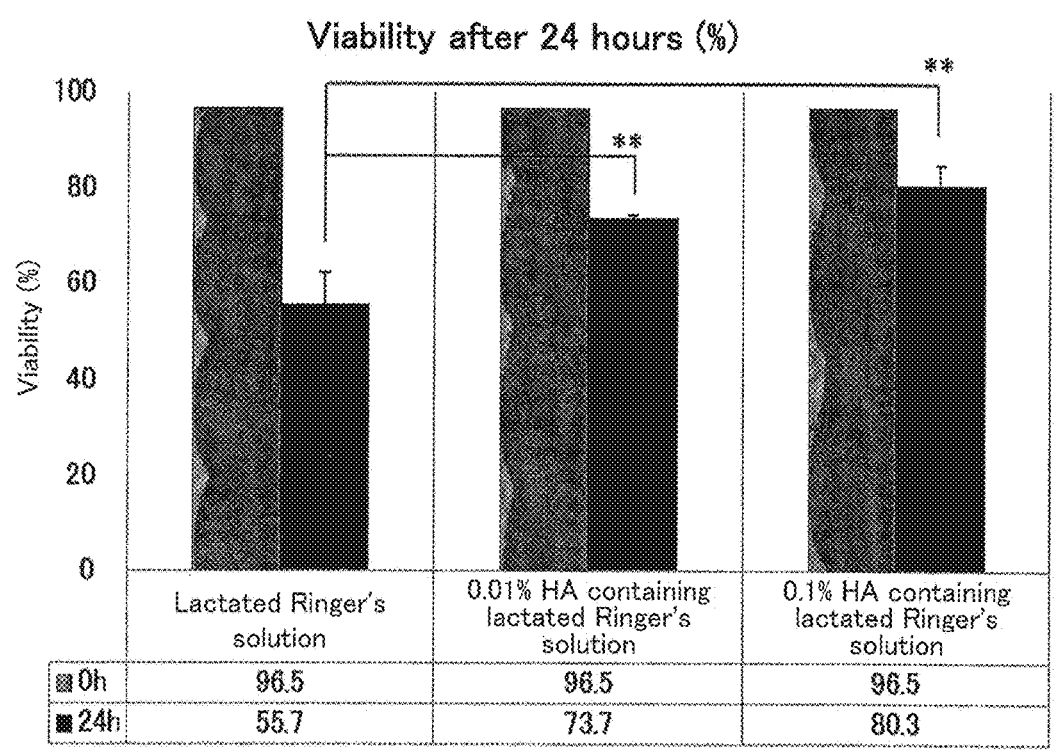
FIG. 28 is a chart showing cell viabilities in cases where 5×10$^5$ MSCs were stored in an incubator at 37° C. for 24 hours, in 3 types of preservative solution: 1 mL of lactated Ringer's; a solution containing 990 µL of lactated Ringer's and 10 µL of 1% hyaluronic acid (hyaluronic acid concentration of the solution: 0.01%); and a solution containing 900 µL of lactated Ringer's and 100 µL of 1% hyaluronic acid (hyaluronic acid concentration of the solution: 0.1%).

FIG. 28 shows a result. The result was subjected to statistical analysis by Non-repeated Measures ANOVA and the mark "**" was provided to parts where a significant difference (P<0.01) was found. In FIG. 28, "HA" represents "hyaluronic acid". It was confirmed as shown in FIG. 28 that, under the storage condition of 37° C., (a) the solution containing 990 μL of lactated Ringer's and 10 μL of 1% hyaluronic acid (hyaluronic acid concentration of the solution: 0.01%) and (b) the solution containing 900 μL of lactated Ringer's and 100 μL of 1% hyaluronic acid (hyaluronic acid concentration of the solution: 0.1%) significantly had a cytoprotective effect, as compared to (c) 1 mL of lactated Ringer's solution.

From the above result, it was found that even when the cytoprotective agent is provided in the form of a preservative solution prior to administration of cells and a concentration of the cytoprotective agent in the preservative solution is 0.01% to 0.1%, the cytoprotective agent still has a cytoprotective effect and allows a long-term storage of the cells particularly under a refrigerated condition. Further, the result also showed that the viability after 24 hours is high under the storage condition of 37° C. at which the cells are considered to have a high metabolic activity. This indicated that the cytoprotective agent has a high cytoprotective effect even in a case where the cells are put under a high temperature condition in transportation or storage.

INDUSTRIAL APPLICABILITY

The present invention can provide a safer and highly useful articular damage treatment agent which uses mesenchymal stem cells. Accordingly, the present invention is applicable to cartilage-tissue regenerative medicine using mesenchymal stem cells. Further, it has been found that the present invention makes it possible to store cells for a long term because of a cytoprotective effect. Therefore, the present invention can be applied, as a cytoprotective agent or the like, to the field of regenerative medicine industry.

The invention claimed is:

1. A method for producing a cartilage-damage treatment agent, comprising the steps of:
   (i) proliferating mesenchymal stem cells in a serum-free medium A containing an FGF, a PDGF, a TGF-β, an HGF, an EGF, at least one phospholipid and at least one fatty acid; and
   (ii) mixing the mesenchymal stem cells thus proliferated in the step (i), an isotonic preserving agent, wherein the isotonic preserving agent is lactated Ringer's solution, and hyaluronic acid as a cytoprotective agent,
   wherein in the step (ii), the hyaluronic acid is mixed so that a concentration of the hyaluronic acid is 0.005% or more and 0.01% or less,
   wherein in the step (ii), the mesenchymal stem cells are mixed so that the number of the mesenchymal stem cells is $1 \times 10^6$ cells/mL or more and $1 \times 10^7$ cells/mL or less,
   wherein the cartilage-damage treatment agent maintains a viability of the mesenchymal stem cells of 70% or more up to 5 weeks at 4° C.

2. The method according to claim 1, wherein in the step (ii), the hyaluronic acid is mixed so that a concentration of the hyaluronic acid is 0.01% or more and 0.1% or less.

3. The method according to claim 1, wherein the mesenchymal stem cells are derived from a tissue selected from the group consisting of synovial membrane, umbilical cord, cord blood, amnion, bone marrow, and an adipose tissue.

4. The method according to claim 1, wherein in the step (i), the mesenchymal stem cells are proliferated while a differentiation ability of the mesenchymal stem cells is maintained.

5. The method according to claim 1, further comprising the step of pre-proliferating the mesenchymal stem cells in a serum-free medium B which is different from the serum-free medium A, said serum-free medium B containing an FGF, a PDGF, an EGF, at least one phospholipid, and at least one fatty acid, prior to the step (i).

* * * * *

UNITED STATES PATENT AND TRADEMARK OFFICE
CERTIFICATE OF CORRECTION

PATENT NO. : 10,507,266 B2
APPLICATION NO. : 14/906495
DATED : December 17, 2019
INVENTOR(S) : Koichiro Tsuji et al.

It is certified that error appears in the above-identified patent and that said Letters Patent is hereby corrected as shown below:

In the Claims

Column 38, Claim 1, Line 20 reads:
cells is $1 \times 10^6$ cells/mL or more and $1 \times 10'$ cells/mL or Whereas it should read:
cells is $1 \times 10^6$ cells/mL or more and $1 \times 10^7$ cells/mL or Signed and Sealed this
Fifth Day of May, 2020

Andrei Iancu
*Director of the United States Patent and Trademark Office*